(12) United States Patent
Goble

(10) Patent No.: US 6,843,789 B2
(45) Date of Patent: Jan. 18, 2005

(54) ELECTROSURGICAL SYSTEM

(75) Inventor: Colin C. O. Goble, Surrey (GB)

(73) Assignee: Gyrus Medical Limited, Cardiff (GB)

( * ) Notice: Subject to any disclaimer, the term of this patent is extended or adjusted under 35 U.S.C. 154(b) by 160 days.

(21) Appl. No.: 10/186,710

(22) Filed: Jul. 2, 2002

(65) Prior Publication Data

US 2002/0165531 A1 Nov. 7, 2002

Related U.S. Application Data

(63) Continuation-in-part of application No. 09/984,252, filed on Oct. 29, 2001.
(60) Provisional application No. 60/255,775, filed on Dec. 18, 2000.

(30) Foreign Application Priority Data

Oct. 31, 2000 (GB) ............................................. 0026586
Apr. 29, 2002 (GB) ............................................. 0209772

(51) Int. Cl.⁷ ............................................. A61B 18/12
(52) U.S. Cl. ........................................ 606/41; 606/49
(58) Field of Search ................................... 606/32–52

(56) References Cited

U.S. PATENT DOCUMENTS

| | | |
|---|---|---|
| 3,685,518 A | 8/1972 | Beuerle et al. |
| 4,038,984 A | 8/1977 | Sittner |
| 4,492,231 A | 1/1985 | Auth |
| 4,517,976 A | 5/1985 | Murakoshi et al. |
| 4,727,874 A | 3/1988 | Bowers et al. |
| 5,346,491 A | 9/1994 | Oertli |
| 5,423,810 A | 6/1995 | Goble et al. |
| 5,445,638 A | 8/1995 | Rydell et al. |
| 5,496,312 A | 3/1996 | Klicek |
| 5,757,445 A | 5/1998 | Vu et al. |
| 5,885,281 A | 3/1999 | Urueta |
| 6,033,399 A | 3/2000 | Gines |
| 6,059,783 A | 5/2000 | Kirwan, Jr. |
| 6,228,080 B1 | 5/2001 | Gines |
| 6,296,636 B1 | 10/2001 | Cheng et al. |
| 6,398,779 B1 | 6/2002 | Buysse et al. |
| 6,733,498 B2 | 5/2004 | Paton et al. |

FOREIGN PATENT DOCUMENTS

| | | |
|---|---|---|
| EP | 0 247 717 A2 | 12/1987 |
| EP | 0 754 437 A2 | 1/1997 |
| EP | 1 053 719 A1 | 11/2000 |
| EP | 1 053 720 A1 | 11/2000 |
| WO | WO 96/14021 | 5/1996 |
| WO | WO 97/24073 A1 | 7/1997 |
| WO | WO 99/20213 | 4/1999 |
| WO | WO 00/54683 | 9/2000 |
| WO | WO 02/36028 A1 | 5/2002 |

Primary Examiner—Roy D. Gibson
Assistant Examiner—Aaron Roane
(74) Attorney, Agent, or Firm—Oliff & Berridge, PLC

(57) ABSTRACT

An electrosurgical system has an electrosurgical generator and a bipolar electrosurgical instrument, the generator being arranged to perform a treatment cycle in which radio frequency energy is delivered to the instrument as an amplitude-modulated radio frequency power signal in the form of a succession of pulses characterized by successive pulses of progressively increasing pulse width and progressively decreasing pulse amplitude. There are periods of at least 100 milliseconds between successive pulses, and the treatment cycle begins with a predetermined pulse mark-to-space ratio. Energy delivery between pulses is substantially zero. Each burst is of sufficiently high power to form vapor bubbles within tissue being treated and the time between successive pulses is sufficiently long to permit condensation of the vapor.

25 Claims, 10 Drawing Sheets

-×- 200W @ 15%DUTY WITH 4 AMPS
—✕— 30W CONTINUOUS

Fig. 18
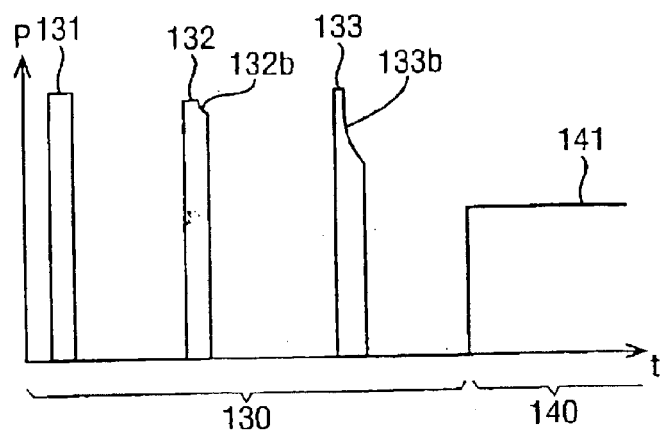
Fig. 19
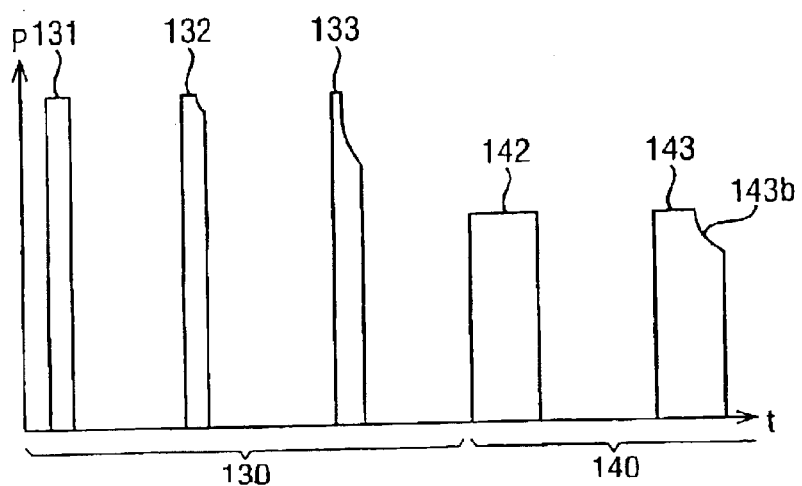
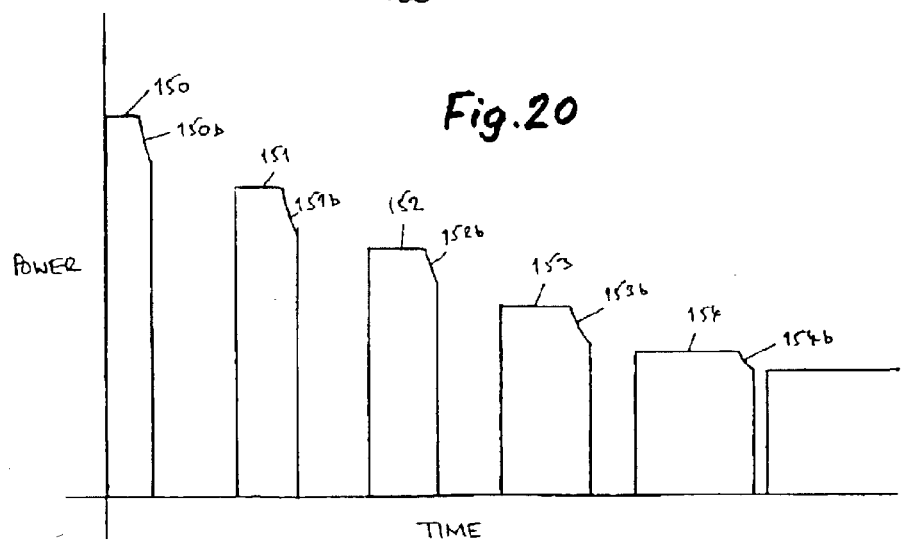
Fig. 20

ELECTROSURGICAL SYSTEM

This is a Continuation-in-Part of application Ser. No. 09/984,252 filed Oct. 29, 2001, which in turn is a Non-Provisional of Provisional Application No. 60/255,775 filed Dec. 18, 2000. The entire disclosure of the prior applications are hereby incorporated by reference herein in its entirety.

FIELD OF THE INVENTION

This invention relates to an electrosurgical instrument, to an electrosurgical method and to an electrosurgical system. More specifically, the present invention provides a bipolar radiofrequency (r.f.) electrosurgical output, the characteristics of which produce faster, more controlled and more effective sealing of vascular structures such as might be performed during endoscopic surgery, and the like.

BACKGROUND OF THE INVENTION

The use of r.f. current to effect the cutting and coagulation of body tissues has been known for many years, and comes under the broad description of electrosurgery. Two techniques to deliver the r.f. current to the tissues are in common usage today.

The first of these, monopolar electrosurgery, involves the use of an active (tissue treatment) electrode and a remote return (or neutral) electrode (or pad) placed on an external surface of the patient's body. Current flows from the active electrode, through the target site, and through any other tissue lying in the path between the target site and the return electrode. This arrangement introduces the potential for off-site burns, in other words tissue burns occurring at sites other than the target site. The medical literature includes references to numerous instances of capacitive coupling of the r.f. current to other instruments causing burns, direct coupling to tissue due to insulation failure, burns along the current path through the patient's body, and those occurring at the site of application of the return pad.

The second technique is known as bipolar electrosurgery. Bipolar electrosurgery involves the containment of current flow local to a target site by incorporating both the active and return electrodes close together, typically at the tip of the surgical instrument. This arrangement avoids the need for current flowing through the body to complete the electrical circuit, and hence eliminates the risks of off-site burns. The use of bipolar electrosurgery is, therefore, preferred where safety is of greatest concern, particularly when applying r.f. current close to vital structures, or when visualisation is limited such as during endoscopic surgery. As a result, bipolar coagulation or sealing of vessels during endoscopic surgery has become a cost-effective and easy to use alternative to the mechanical sealing of blood vessels using metal clips, staples or ligatures.

Normally, the electrosurgical instrument used for bipolar coagulation consists of a pair of forceps, in which each jaw of the forceps is an r.f. electrode. Depending on the size of the forceps, and hence the amount of tissue included in the circuit, the applied power can typically vary between 1W and 50W. The most significant problems encountered, when using conventional bipolar r.f. electrosurgery, are related to the distribution of energy throughout the tissue grasped between the forceps. As a result of these limitations, surgeons will commonly apply r.f. energy well beyond that necessary for effectively sealing a blood vessel, in theory to ensure complete sealing and to reduce the risk of bleeding when the vessel is subsequently divided. This leads to an excessive spread of the coagulation to adjacent tissues, and increases the risk of the forceps jaws becoming stuck to the tissue. This sticking can be sufficiently severe to cause coagulated tissue to be torn away when releasing the forceps, leading to damage of untreated areas of the vessel, and significant bleeding.

The industry standard for the coagulation output of a bipolar r.f. electrosurgery generator is a maximum power in the region of 50W–70W, with a specified load curve between 10 ohms and 1000 ohms. This power is normally delivered as a continuous, low crest factor waveform such as a sine wave. Peak voltages from such a generator can be as high as 1000V peak-to-peak. It has now been recognised, however, that lower voltages reduce the propensity to stick or carbonise the tissue when coagulating. Maximum voltages of up to 400V peak-to-peak are now more usually used in modern designs. The low impedance matching capability of this type of generator is limited, with maximum current delivery typically being in the region of 1.5A at full power.

Despite these advances, none of the known bipolar r.f. generators overcomes the problems of differential energy absorption within the tissue due to the variation in tissue impedance, the geometry of the forceps jaws, the presence of conductive fluids and tissue compression. As a result, coagulation is inevitably taken to the desiccation point, at which the tissue becomes dried out as fluids are boiled off, with an attendant elevation in the temperature of the forceps jaws. The cause of tissue sticking is the elevation in electrode temperature above 70–80° C. As this is more likely to occur because of the variables encountered during use, it is particularly likely to occur when the vessel to be treated is contained within the high impedance of a fatty layer, as is commonly encountered in vascular pedicles. The fatty layer effectively insulates the lower impedance vascular structure, so that incomplete sealing and excessive application are both more likely to occur.

For these reasons, it would be desirable to deliver bipolar r.f. electrosurgical energy in an improved way for coagulating tissues. It would be particularly desirable to provide more controlled absorption of energy throughout the tissue to be treated, largely irrespective of variables encountered during use, so that the problems of incomplete vessel sealing within fatty pedicles, tissue sticking and excessive thermal margin can be overcome. It would further be desirable to provide an improved bipolar r.f. electrosurgical output through an instrument such as that disclosed in U.S. Pat. No. 5,445,638 during endoscopic surgery.

Electrosurgical instruments have been proposed to resolve the problems of sticking. U.S. Pat. Nos. 3,685,518, 4,492,231 and 6,059,783 all describe methods of heat removal by constructing the electrodes of sufficient-thermal capacity, and/or by the use of thermally-conductive materials to dissipate heat. U.S. Pat. No. 5,885,281 describes the use of coatings to minimise the effects of sticking.

Impedance and temperature-based r.f. generator control is described in U.S. Pat. No. 5,496,312. Our U.S. Pat. No. 5,423,810 describes an impedance-controlled, bipolar cauterising output based on variations in the oscillator carrier frequency according to tissue impedance.

U.S. Pat. No. 6,033,399 discloses an electrosurgical generator capable of applying output power to surgical graspers in a manner such that the power level varies cyclically between low and high values in response to the changing impedance of the grasped tissue being treated, until the tissue is fully desiccated.

These techniques have had moderate success in terms of preventing sticking. One method of counteracting the negative temperature coefficient of resistance (NTCR) effect which tissue exhibits during coagulation is to introduce a positive temperature coefficient of resistance (PTCR) material, which new material is dominant. PTCR material produces the opposite effect to current hogging so that, instead of current hogging, the predominant effect would then be one of current sharing. Whilst it might be possible to coat the electrodes with a PTCR material, the material would dissipate heat and heat up the electrodes. Alternatively, a dielectric layer could be introduced with a positive temperature coefficient of impedance. This has the attraction of little or no heat dissipation, but unfortunately is very difficult to realise due to the lack of suitable materials.

SUMMARY OF THE INVENTION

According to a first aspect of the invention, an electrosurgical generator comprises a source of r.f. energy, at least a pair of output terminals for connection to a bipolar electrosurgical instrument and for delivering r.f. energy from the source to the instrument, and a pulsing circuit for the source, wherein the pulsing circuit and the source are so arranged as to deliver into a resistive load, when connected across the output terminals, an amplitude-modulated r.f signal at the output terminals in the form of a succession of pulses which is characterised by successive pulses being of decreasing power amplitude and of increasing pulse width. Preferably, the increase in the pulse width of successive pulses is related to the decrease in amplitude. This may be such that the energy delivered in each pulse is substantially fixed from pulse to pulse over at least a major part of the succession of pulses. The decrease in pulse amplitude and the increase in pulse width may be effected by control circuitry which includes a sensor circuit for monitoring at least one electrical parameter associated with the output terminals, so that the pulse amplitude and pulse width are controlled according to the monitored electrical parameter. Preferred electrical parameters in this respect include the load resistance and, in the case where the r.f. voltage applied to the load is limited to a predetermined maximum value, the time from the start of a respective pulse to the instant at which the peak voltage reaches the predetermined maximum value. Generally, the maximum value is below 200V peak and is preferably in the range of from 50V peak to 200V peak.

Typically, the pulse repetition rate is less than or equal to 5 Hz and is preferably less than 11 Hz, the r.f source and the pulsing circuit being arranged to generate a succession of treatment pulses of r.f. energy at the output terminals with the periods between successive such pulses being 100 ms, preferably 300 ms or longer. Between the pulses the delivered power is preferably substantially zero.

In the case of the pulse repetition rate being less than 1 Hz, the pulsing circuit and the r.f. source are arranged to generate a succession of treatment pulses of r.f. energy at the output terminals, the periods between successive such pulses being 1 second or longer.

Typically, each pulse of the succession of pulses delivers at least 2 joules of r.f. energy when the load resistance is in the range of from 10 $\Omega$ to 1 k$\Omega$.

The treatment cycle may commence with a succession of pulses, as described above, followed by a period of continuous energy delivery, which may be at least 1 second in duration.

Additional preferred features are contained in the accompanying dependent claims.

According to a further aspect of the invention, an electrosurgical generator comprises a source of r.f energy, at least a pair of output terminals for connection to a bipolar electrosurgical instrument and for delivering r.f. energy from the source to the instrument, and a pulsing circuit for the source, wherein the pulsing circuit and the source are so arranged as to deliver into a resistive load, when connected across the output terminals, an amplitude and modulated r.f. power signal in the form of a succession of pulses having a pulse duty cycle which increase progressively. Progressive increase is accompanied by progressive decrease in peak power. Indeed, the increase in peak power may be such that the average delivered power over a treatment cycle remains substantially constant. The generator preferably includes a sensing circuit associated with the output terminals for sensing the above-mentioned electrical parameter. The pulsing circuit may then be arranged automatically to adjust the duty cycle of the signal pulses in response to the sensed electrical parameter. The sensing circuit may, alternatively, or additionally, be arranged to be responsive to an identification element housed in an instrument connected to the output terminals. It may be arranged to detect an initial value of load impedance associated with the start of the treatment cycle, the pulsing circuit preferably being arranged such that the initial pulse duty cycle increases with increasing sensed initial load impedance.

The invention also includes a method of electrosurgically coagulating tissue between the electrodes of a bipolar electrosurgical instrument, in which r.f. energy are applied to the tissue via the electrodes in a succession of pulse bursts of progressively increasing length and progressively decreasing amplitude. Typically, the increase in the length of successive bursts is related to the decrease in amplitude of those bursts.

According to another aspect of the invention, there is provided an electrosurgical system comprising the combination of an electrosurgical generator as described above, together with a bipolar electrosurgical instrument coupled to an output of the generator. The instrument may be a pair of forceps. In addition, the instrument is preferably removably connectible to the generator and includes an instrument identification element, as mentioned above. The system may comprise the generator together with a plurality of bipolar electrosurgical forceps instruments which are selectively connectible to the generator, each containing respective different identification elements. The electrodes of the instruments define different tissue contact areas, the respective identification elements being arranged to co-operate with the sensing circuit and/or the pulsing circuit so as to set the pulse width or pulse duty cycle to a lower value for an instrument with electrodes defining a comparatively large tissue contact area and to a higher value for an instrument with electrodes defining a comparatively small tissue contact area. Additionally or alternative, the sensing circuit and/or the pulsing circuit are selected and configured in combination with the identification elements to decrease the pulse frequency when an instrument with a comparatively large tissue contact area is selected.

According to yet another aspect of the invention, an electrosurgical generator comprises a source of r.f. energy, at least a pair of output terminals for connection to a bipolar electrosurgical instrument and for delivering r.f. energy from the source to the instrument, and a pulsing circuit for the source, wherein the pulsing circuit and the source are arranged to deliver into a resistive load across the output terminals an amplitude-modulated r.f signal at the output terminals in the form of a succession of pulses characterised by the periods between successive pulses in the signal being at least 100 ms and by a predetermined mark-to-space ratio.

Preferably, the depth of amplitude modulation is substantially 100%, with a pulse mark-to-space ratio of less than 1:1.

When a resistive load is coupled across the output terminals of the generator, the r.f. current during each of a number of successive pulses may reach at least 3 amps r.m.s.

In one preferred generator in accordance with the invention, the circuitry is arranged such that the peak voltage of the amplitude-modulated r.f. signal remains below 200 volts when a resistive load is connected across the output terminals, the r.f. energy delivered in each pulse being at least 2 joules when the resistive load is in the range of from 10 Ω to 1 kΩ.

According to an additional aspect of the invention, an electrosurgical generator comprises a source of radio frequency (r.f.) energy, at least a pair of output terminals for connection to a bipolar electrosurgical instrument and for delivering r.f. energy to the instrument, a pulsing circuit for the source, and control circuitry including means for monitoring at least one electrical parameter associated with the output terminals, wherein the arrangement of the control circuitry, the pulsing circuit and the source is such that, with the output terminals connected to a resistive load, the control circuitry causes the source to deliver into the load an amplitude-modulated r.f. power signal which, at least in an initial period, is a succession of pulses with a predetermined initial pulse duty cycle and, in a subsequent period, has a different characteristic, the transition from the initial period to the subsequent period being controlled by the control circuitry in response to the at least one monitored parameter. The control circuitry may be arranged to cause the r.f. power signal, during the subsequent period, to provide continuous energy delivery or more nearly continuous energy delivery than during the initial period but, more commonly, the r.f. power signal is delivered as an amplitude-modulated signal which, during at least part of the above-mentioned subsequent period, has a second predetermined pulse duty cycle which is greater than the initial pulse duty cycle. Generally, the peak power during the subsequent period is less than during the initial period. In one particular preferred embodiment, the pulse duty cycle is fixed at a first predetermined pulse duty cycle during the initial period and at a second, greater predetermined pulse duty cycle during the subsequent period, the subsequent period following the initial period directly. As an alternative, the pulse duty cycle of the r.f. power signal may increase in more than one step so that, for instance, the signal starts with a low predetermined and fixed pulse duty cycle, then is switched to a pulse duty cycle which is greater than the first pulse duty cycle and with lower peak power and, subsequently, to a yet higher pulse duty cycle and yet lower peak power. As a further alternative, the pulse duty cycle may increase progressively, accompanied by progressively reducing peak power.

In this case, whether the treatment cycle performed using the r.f. power signal is a pulse signal followed by a continuous-wave (c.w.) signal, or a signal in which the pulse duty cycle is increased stepwise or progressively, the peak power may be correspondingly reduced such that the average delivered power remains approximately constant over the majority of the treatment cycle, the cycle commencing with the initial period and ending when the r.f. power signal is terminated.

The transition from the initial period to the subsequent period may be controlled in response to a feedback signal representative of energy delivered into a resistive load, or one which is representative of the resistance or impedance of the load. A feedback signal may be obtained by sensing the output voltage (peak voltage or r.m.s. voltage), the transition being controlled in response to a sensing signal from a sensing circuit indicative of the output voltage exceeding a predetermined value, for instance. The predetermined value may be in the region of 150V to 250V peak.

In the case of the generator having a switched mode power supply operating at a power supply switching frequency, the output voltage sensing circuit may be coupled to the power supply in such a way that when the output voltage exceeds a predetermined value, pulsing of the power supply is halted. The output voltage may then be sensed by monitoring the driving pulses of the power supply, e.g. by counting the pulses. The counting output may then be used to control the pulse duty cycle and/or peak power of the r.f. power signal.

According to yet an additional aspect of the invention, a method of electrosurgically coagulating tissue between the electrodes of a bipolar electrosurgical instrument comprises the application of r.f. energy to the tissue via the electrodes in a succession of pulse bursts with a duty cycle of 40% or less, wherein the instantaneous r.f. current at the start of each successive burst is higher than the instantaneous r.f. current at the end of the previous burst.

A further aspect of the invention provides an electrosurgical system comprising an electrosurgical generator and a bipolar electrosurgical instrument coupled to an output of the generator, the generator being such as to provide a succession of controlled bursts of electrosurgical energy to the instrument at a predetermined pulse mark-to-space ratio, wherein each burst has a sufficiently high power to form at least one vapour bubble within tissue being treated by the instrument, and the time duration between successive bursts is sufficiently long to permit recondensation of the or each vapour bubble, the peak delivered power being between the bursts being substantially zero. The time delay duration is generally at least 100 milliseconds and the generator preferably has other features already mentioned.

The invention also includes an integrated electrosurgical generator and instrument system, wherein the generator has the features referred to above and the instrument comprises a pair of forceps.

According to yet a further aspect of the invention, there is provided an integrated electrosurgical generator and instrument system, when the instrument is removably connectible to the generator and includes an instrument identification element. The generator may have any of the above-mentioned generator features and includes a sensing circuit for sensing the identification element, the pulsing circuit of the generator being arranged automatically to adjust the mark-to-space ratio of the signal pulses in response to the identification element as sensed by the sensing circuit. The system may include a plurality of bipolar forceps instruments which are selectively connectible to the generator and contain respective identification elements. The instruments have different tissue contact areas (defined by the instrument electrodes) and the identification elements are selected such that, in combination with the sensing circuit and/or the pulsing circuit of the generator, the mark-to-space ratio is set to a lower value for an instrument with electrodes defining a comparatively large tissue contact area and to a higher value for an instrument with electrodes defining a comparatively small tissue contact area. The identification elements, the sensing circuity and the pulsing circuit are preferably selected and configured to decrease the pulse frequency when an instrument with a comparatively large tissue contact area is selected.

Yet another aspect of the invention provides a method of electrosurgically coagulating tissue between the electrodes of a bipolar electrosurgical instrument in which controlled bursts of r.f. energy are applied across the electrodes, each burst being of sufficiently high power to form at least one vapour bubble within the tissue, and the time duration between successive bursts is sufficiently long to permit recondensation of the or each bubble.

The tissue behaves as a positive temperature coefficient of resistance (PTCR) material by the application of r.f. energy at high power across the electrodes of a bipolar instrument. The PTCR effect is produced by exploiting the tendency for "current hogging" whereby, due to a negative temperature coefficient resistance (NTCR), the application of r.f. energy to a region of tissue causes local temperature increases which, in turn, causes localisation of current density, the r.f. current tending to be concentrated at the areas of highest temperature, especially when, for instance, a thin section of tissue is grasped between electrodes formed as a pair of forceps. The PTCR effect is achieved by delivering sufficient power to the tissue that a vapour bubble is formed which, providing the applied voltage is substantially below 300 volts peak, is substantially an electrical insulator. Since, now, the r.f. current must find paths around the vapour bubble, the material as a whole has exhibited a rise in impedance, effectively giving a PTCR characteristic. The dissipation of energy is thus more evenly distributed and thermal coagulation occurs throughout the target tissue as a result.

A notable feature is that the highest temperatures, induced by the highest current densities, occur within rather than on the surface of the tissue between the instrument electrodes.

Once vapour is formed, the highest current densities occur around the edges of the vapour bubbles, causing further heating and expansion of the vapour bubble until the end of the respect pulse burst, as expansion of the bubbles being such that the areas of highest current density are forced into untreated regions of tissue below the tissue surfaces. This reduces the risk of localised heating of the forceps jaws and hence reduces the risk of tissue sticking.

These effects result in preferential and more uniform distribution of energy dissipation within the target tissue to provide a method of treating tissue whereby a lateral margin of thermal effect is reduced and further that the coagulating effect on blood vessels can be obtained throughout other support tissues such as fatty connective tissue. A further resulting advantage is that the surgeon is provided with a more repeatable end-point of coagulation treatment despite the variable conditions which may be encountered.

The control of the tissue effect may be obtained by altering the pulse characteristics depending on the specific instruments connected to the generator with the effect of reducing the variables encountered during use. It is also possible to reduce the variables in the case of a forceps instrument embodiment by controlling the closure force exerted on the tissue.

In this connection and as described, the generator pulsing circuit may be arranged automatically to adjust the mark-to-space ratio of the signal pulses in response to a sensing circuit associated with the output terminals. The sensing circuit may be arranged to be responsive to an identification element, such as an element having a particular impedance, housed in an instrument connected to the output terminal. Alternatively, the sensing circuit may be arranged to detect an initial value of a load impedance between the output terminals, which value is associated with the start of r.f. energy application, the pulse characteristics being set according to the initial load impedance value for the duration of a treatment operation comprising a succession of the pulses. Typically, the pulsing circuit is arranged such that the initial pulse mark-to-space ratio increases with increasing sensed initial load impedance. In addition, the pulsing circuit may be arranged to adjust peak power in response to the sensing circuit, the set peak power decreasing as the sensed initial load impedance increases. The pulse frequency may also be adjusted by the pulsing circuit in response to the sensing circuit, the pulse frequency being increased with increasing sensed initial load impedance.

In the case of the instrument (which can include the connecting cable and its connector) containing an identification element such as a capacitor, resistor, or other coding element, the mark-to-space ratio may be set according to the tissue contact areas of the electrodes, such that instruments with larger tissue contact areas cause the generator to be set with a comparatively low mark-to-space ratio.

The invention will be described below in greater detail, by way of example, with reference to the drawings.

BRIEF DESCRIPTION OF THE DRAWINGS

In the drawings:

FIGS. 18 and 19 are graphs showing the variation of delivered power with time in second and third embodiments of the invention, and FIG. 20 is a graph showing the variation of delivered power with time in a fourth preferred embodiment of the invention.

DETAILED DESCRIPTION OF THE PREFERRED EMBODIMENT OF THE INVENTION

Figure 1:
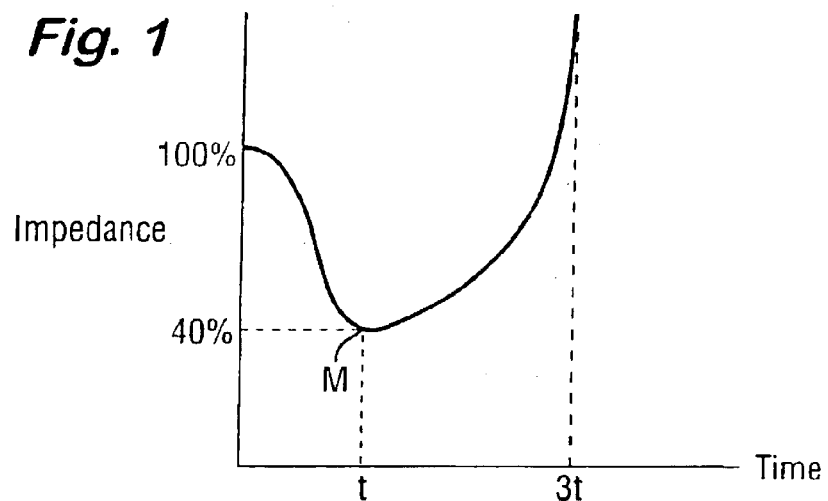
FIG. 1 is a graph illustrating the ideal behaviour of tissue impedance against time during the application of bipolar r.f. energy.

Referring to the drawings, FIG. 1 is a graph showing the ideal behaviour of tissue impedance against time during the application of bipolar r.f. energy. The impedance is seen to fall during the initial phase of application as a result of heating of electrolytes in the vicinity of the tissue being treated. A minimum M is reached, following which the impedance begins to rise as the tissue is desiccated and becomes less conductive. Treatment, in terms of coagulation of the tissue, optimally occurs around the point M of minimum impedance. Continued delivery of energy beyond this point M merely serves to increase the lateral margin, to increase the temperature of the application electrodes, typically a pair of forceps jaws, due to increased steam generation and to increase the risk of tissue sticking. Increased ion mobility can cause a 60% impedance reduction over a typical temperature change of 37° C. to 100° C. In practice, however, a 60% reduction is never seen since the tissue is never at a uniform temperature.

Figure 2:
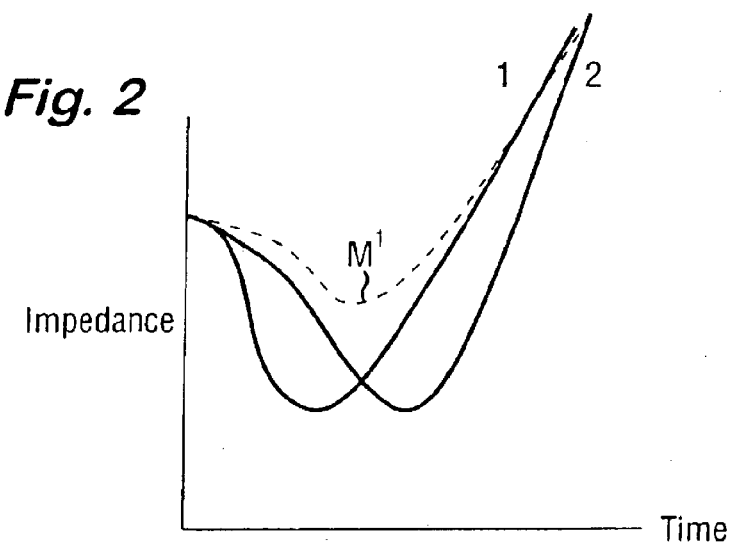
FIG. 2 is a graph illustrating the compound behaviour of tissue impedance against time as a result of the phenomenon of current hogging.

FIG. 2 is a graph showing two solid line relationships which illustrate how the tissue impedance may change at different points across the contact areas of a typical bipolar forceps. Plot 1 is indicative of a point at which the impedance across the forceps decreases rapidly on application of power, such as that which may occur due to the forceps jaws being closer together at one point along their length. As a result, this point of the contact area will take marginally more power from the common bipolar r.f. power source. This, in turn, will cause heating at this point, with a further lowering of the impedance, and a consequential increase in the power delivered at this point at the cost of other, higher impedance points of contact such as for that point shown in Plot 2. This is the phenomenon known as current hogging, and it is a feature of materials, such as conductive tissue fluids, which exhibit a negative temperature coefficient of resistance (NTCR). These individual characteristics will, of course, not be seen by the common energy source, which will only see the combined effect of the two as indicated by the dotted line.

The first notable feature of the combined effect is that the impedance minimum $M^1$ is less pronounced. The second notable feature is that, when desiccation occurs, the positive rise in impedance with applied power results in the opposite of current hogging, this being known as current sharing. This current sharing results in a convergence of the two plots when desiccation starts to occur. It is for this reason that end-point determination of treatment can only be reliably detected throughout the tissue pedicle once the tissue reaches the point of desiccation, with the attendant unnecessary margin of effect, a hardening of the tissue, and electrode/tissue sticking.

The current hogging phenomenon can be more easily understood by considering two infinitely-small pieces of tissue to which the same power source is applied, i.e. two pairs of electrodes connected in parallel to the same power source and applied to these two microscopic pieces of tissue. If one of these pieces of tissue has a marginally lower impedance than the other, it will take marginally more power. However, this marginal power increase in the lower impedance piece will result in greater heating. Greater heating, as explained above, will result in lower impedance. Thus, the power differential between the two pieces will increase, resulting in an even greater power differential. This is the current hogging phenomenon, and it always happens in materials with a negative temperature coefficient of impedance which, in this instance, constitutes the electrolyte within the tissue. A practical electrode applied to tissue will effectively have an infinite number of tissue sections behaving between these two extremes. As already stated, the electrical characteristics of each of these sections will have a tendency to converge at desiccation. The safest approach is, therefore, to use the point of desiccation as the end point for applied power, and this is easily detectable due to rapidly rising voltage at the output of the generator, or by the lack of activity at the target tissue. However, this gives rise to the four problems mentioned earlier. The surgeon is, therefore, faced with the dilemma of trying to ensure treatment is sufficient to seal vessels, versus the risk of tissue sticking and increasing the lateral thermal margin.

As already stated, the variation over the forceps surfaces is due to initial impedance, temperature, electrical conductivity, tissue thickness and electrode surface area. Most of these variables are highly interactive and, therefore, difficult to isolate. The net effect, however, is one of current hogging and differential energy absorption throughout the tissue included within the grasp of the forceps. This is quite clearly illustrated when using forceps such as those described in the above-mentioned U.S. Pat. No. 5,445,638. The region of coagulation can be seen to start at one end of the forceps and to work its way along. This usually occurs due to the jaws not being parallel when they are closed, such that the coagulation commences in the region of lowest impedance (or closest proximity of the jaws) which will then exhibit the current hogging phenomenon. There is, therefore, a decreased possibility of viable coagulation along the full length of the jaws, without sticking occurring at the point at which coagulation commenced.

Figure 3:
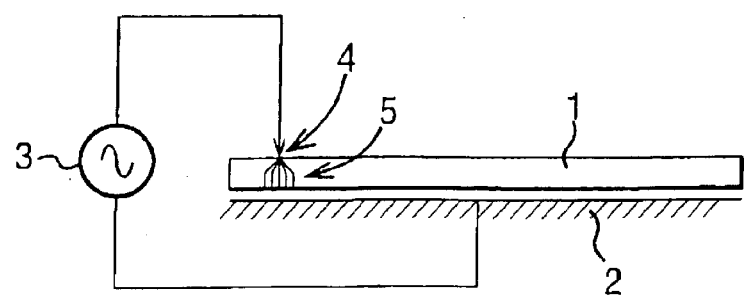
FIG. 3 is a schematic circuit diagram illustrating the current distribution density associated with current hogging when an r.f. source is applied across a laminar section of tissue.

Practical trials show that the thicker the tissue treated, the less the propensity for current hogging. Current hogging occurs due to exclusive current paths. Consider an extreme case of a microscopically-thin layer 1 of tissue something like a postage stamp, with an electrode 2 (shown only schematically) applied to the glue side of the "stamp", such as is illustrated in FIG. 3. If current is passed from an r.f. source 3 through a single point 4 at one corner to the other side, the current will preferentially go directly across the "stamp" to the electrode 2 on the other side. More significantly, no current will travel across the "stamp" in any other region. Thus, an exclusive current path 4 is set up in the tissue. Thin tissue sections, therefore, dramatically increase the propensity for current hogging.

Preventing local temperature rises can reduce the effects of current hogging. As explained earlier, current hogging occurs due to the cyclical cause-and-effect of reduced impedance creating greater heat, causing reduced impedance. Spreading of heat over the contact surfaces will reduce this cyclical event. The heat provided by a low impedance point, if spread, would reduce the impedance of adjacent points; and, therefore, decrease the possibility of current hogging. Using an electrode surface that is highly thermally-conductive can do this, as is taught in the prior art.

Still more attractive is the removal of heat at the tissue/forceps contact surface to prevent the formation of hot spots, so that tissue at the tissue/forceps boundary is kept at a lower temperature, and tissue fluids are prevented from boiling. This measure ensures that maximum temperature rises occur within the tissue pedicle rather than at the surface, resulting in desiccation being limited to within the tissue. Providing forceps jaws with a sufficiently massive thermal heat capacity can achieve this, as is also taught by the prior art.

The fundamental cause of tissue sticking is build-up of heat within the electrodes or forceps jaws. When an electrode reaches temperatures in excess of 80° C., sticking invariably happens, and is worsened when the tissue approaches desiccation. Power delivery after coagulation generates steam that quickly heats up electrodes. The electrodes are exposed to more than three times the energy dissipation to reach desiccation than they, are to reach the pure coagulation point (shown as the minimum M in FIG. 1). Electrodes are therefore, far more likely to reach sticking temperatures when tissue is treated to a desiccation state.

The electrode-to-tissue interface is the energy transfer mechanism to the target tissue. Given a fixed contact area, the electrodes heat up if the electrode-to-tissue contact is in any way electrically resistive, and as a result of thermal conduction from the treated tissue.

In tests using stainless steel or gold electrodes, tissue contact impedance is of the order of 30% lower for gold than for stainless steel. This difference is attributed to the existence of oxide layers on the steel electrode surface. The significance and potential benefit is unknown. This drop would, however, reduce the power dissipation at this point by a corresponding 30%. This is also taught by the prior art, in particular in U.S. Pat. No. 5,885,281.

Obviously, the tissue next to the electrode surface will get hot. Thermal conduction from tissue to the treatment electrodes is dependent on temperature difference and time. The significant factor here is, if the entire volume of treated tissue is in thermal contact with the electrodes, then a much greater proportion of the applied energy is used to heat the electrodes.

As the treatment tissue thickness decreases, a greater proportion of the applied energy causes electrode heating, due to the shorter thermal conduction paths. However, as ever thinner tissue requires less power due to less volume, the two effects tend to cancel one another out, so that electrode temperature as a result of tissue thickness is relatively constant. This, however, makes the assumption that tissue heating is performed uniformly throughout the tissue. In practice, this thin layer of tissue will be particularly susceptible to the occurrence of current hogging and formation of hot spots, due the greater variations in the impedance between the electrodes or forceps jaws. The issue then becomes one of local temperature rises, rather than bulk temperature rises of the electrodes.

Typical bipolar instrumentation designed for endoscopic use is invariably limited in design, due to confines of the access ports. Standard entry port sizes of 5, 7.5 and 10 mm exist. The mechanical aspects of designing such instruments invariably result in hinged designs with a long length to the forceps jaws. Such a design permits maximum tissue engagement with small mechanical movement. As a result of the restricted access, and contrary to the teachings of the prior art, it is desirable to construct forceps with maximum treatment areas for a given thermal mass or size.

One of the commonest design principles employed in bipolar endoscopic instruments is based on the Kleppinger forceps. Rather than using mechanical hinges, the opening of this type of forceps is achieved entirely by a spring force acting on the forceps jaws. Closure is effected by sliding an outer tubular structure over the proximal spring portion of the jaws. The forceps jaws are necessarily quite thin, so as to limit the forces needed to operate them. As a result, the jaws provide negligible heat sinking for the given contact surfaces. The mechanical and biocompatibility properties of such tissue contact parts also tend to result in the use of materials such as stainless steel, further reducing the capacity of the jaws to sink heat developed during delivery of bipolar r.f. energy. The jaws and the proximal sprung area carry r.f. power, and the proximal portion is normally insulated using a plastics coating which further reduces the heat sinking capabilities.

Another exemplary forceps design based on the Kleppinger operating principle is described in U.S. Pat. No. 5,445,638 (Rydell et al) and the commercial product based on this patent is sold by Everest Medical Corp., Minneapolis, USA as the BiCOAG Cutting Forceps. This forceps design includes the additional feature of a blade which may be advanced along a space provided around the longitudinal axis of the forceps jaws such that, once the tissue pedicle is coagulated, it may then be divided without needing a second instrument. The space requirement for operation of the blade yet further reduces the thermal mass and heat sinking capabilities of the forceps jaws. The opposing surfaces of the forceps jaws commonly have teeth to prevent tissue slipping within the grasp of the instrument, particularly during the advancement of the blade. For these teeth to provide simultaneous electrosurgical and grasping functions, they have to mesh as they would between two gear wheels. This arrangement prevents the teeth from piercing the tissue and shorting out the r.f delivery. Unfortunately, the teeth have the effect of increasing the treatment area of the surfaces of the forceps jaws, and increasing the thermal transfer from the tissue to the jaws. The best grasping function is achieved when the teeth are sharp, a feature that the prior art teaches against, as it increases current density at the points of the teeth.

We aim to overcome these limitations in forceps or other bipolar electrode designs by using high power pulses of bipolar r.f energy to convert the NTCR behaviour of tissue to a PTCR behaviour. A natural PTCR effect is realised by exploiting the current hogging phenomenon to the extreme.

Figure 4A:
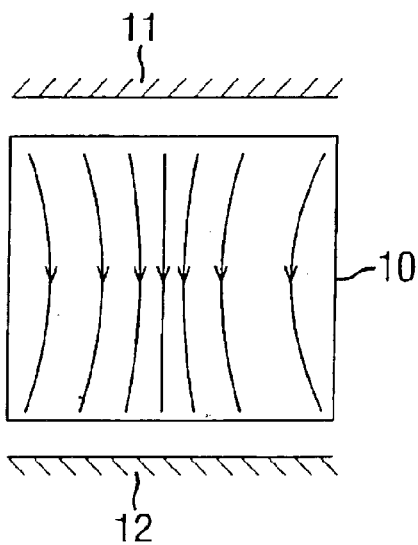
FIGS. 4A–4D are schematic diagrams illustrating variations in current density when a vapour bubble is formed within a laminar section of tissue.
Figure 4B:
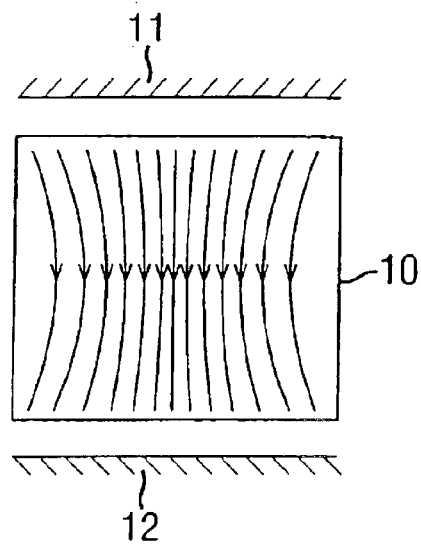
Figure 4C:
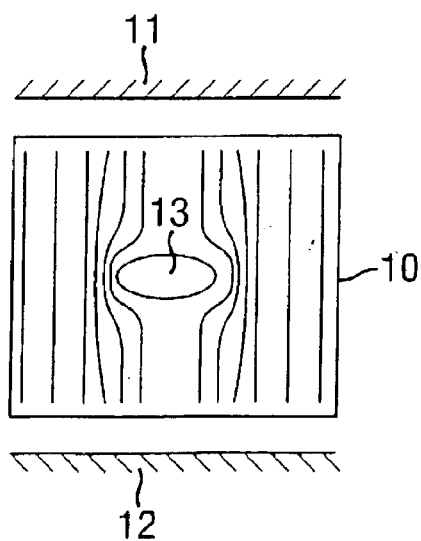
Figure 4D:
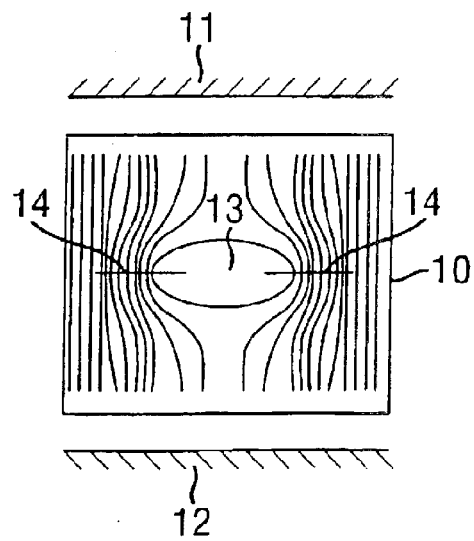

Referring to FIGS. 4A to 4D, if high power is delivered, e.g. at a frequency in the range of from 100 kHz to 500 kHz, to tissue 10 contained between the two contact surfaces (electrodes) 11 and 12 of a bipolar instrument, current hogging ensues, as is illustrated in FIGS. 4A and 4B. Thus, FIG. 4A illustrates initial power delivery to the electrodes 11 and 12 with a low resistance region in the tissue resulting in uneven current density, and FIG. 4B illustrates the increased current density which results from current hogging. If the power is sufficiently high, then a vapour bubble 13 is formed within the tissue due to local temperature, as illustrated in FIG. 4C. This vapour bubble 13 contains pure steam which, at voltages substantially below 300V peak, is completely insulating. The high current density across a region of the tissue created by the current hogging phenomenon is, thereby, defeated by the insulative barrier of the vapour. The growth of the vapour bubble 13 is sustained by regions of high current density at regions 14 which occur at the periphery of the vapour bubble and are along a line perpendicular to the current flow, as illustrated in FIG. 4D. In effect the region of high current density is forced outwards by vapour propagation. If this growth in the vapour bubble 13 was allowed to continue, it would lead to an explosive popping, which could damage tissue outside the immediate application site. In fact, then, one of the principal factors limiting the power which can be applied using a bipolar r.f instrument/generator combination is steam bubble popping, an undesirable effect since it can prevent sealing.

By delivering high power only intermittently, sufficient time is allowed between activations to allow the vapour bubble to condense thereby to alleviate the pressure build up due to boiling of electrolytes. Another advantage of intermittent power delivery is that the clinical effect is slowed, ameliorating the difficulty in detecting and controlling the application of electrosurgical power to an optimum level. (For these reasons, power delivery in the prior art is usually restricted to a rate consistent with an application time in the region of five to ten seconds, with the result that prolonged application of power creates thermal damage adjacent the treatment site.)

An advantage of this technique is that current hogging to the extent of drawing significant current (due to a singular current hogging point) is avoided. The preferred system produces multiple hot spots within a single burst, requiring the bipolar r.f. energy to be of a high current which, typically for a 5 mm laparoscopic BiCOAG Cutting Forceps, has been found to be in excess of 1.5A; and, for a 10 mm version, up to 4A.

Another benefit of high power bursts is that the thermal conduction from heated tissue to the forceps 11, 12 is limited. When the vapour bubble 13 is formed, there is a higher power density within the tissue than at the forceps/tissue interface. This higher power density is the result of more protracted current pathways caused by multiple vapour bubbles. Tissue sub-surface to the forceps jaws, therefore, has a higher effective resistivity. More power is delivered to sub-surface tissue by virtue of higher voltage with less current, and so the tissue adjacent to the electrodes 11, 12 undergoes less heating. During experimentation, tissue pedicles treated in this way show evidence of desiccation inside, but not on the surface. This finding is very different from conventional bipolar r.f. electrosurgical power delivery, as the highest current densities normally occur at the tissue surface in contact with the forceps jaws.

The duty cycle of energy delivery can be adjusted to achieve the best clinical effect. When energy is delivered to tissue in this way, the burst is of sufficient magnitude to cause vapour formation at multiple sites within the tissue. In practical experimentation, the tissue is seen to swell with each burst as evidence of this. Power delivery then ceases before the vapour assumes a sufficiently high pressure to burst the tissue. The subsequent "off" period has to be long enough to ensure thermal relaxation. During this relaxation period, vapour recondenses, and aids the thermal conduction mechanism by condensing preferentially at the coolest point. Moisture within the tissue is thus redistributed by this mechanism. The "off" time, the resultant thermal relaxation and the redistribution of moisture results in new current hogging points being created with each successive burst, ensuring an even distribution of effect in the tissue contained between the electrodes 11, 12.

One of the difficulties associated with power delivery is the range of impedances encountered during use. Typical impedances can range anywhere between 10 ohms and 200 ohms. The maximum applied voltage is limited to a predetermined peak level which prevents arc propagation within the vapour. The peak voltage is, therefore, maintained below 200V, e.g. using a voltage clamp circuit. For maximum power delivery with this ceiling voltage, the waveform needs to be of low crest factor, typically less than 1.5. The most practical low crest factor waveform is a sine wave with a crest factor of 1.4. The maximum r.m.s. voltage is, therefore, 140V r.m.s. The maximum initial power delivery could, therefore, range between 100W and 2000W.

Instrument design can, however, limit maximum power delivery. Heating of the instrument as a result of resistive losses should to be avoided as far as possible. Generally, the thinner the tissue grasped between the forceps jaws of a given area, the lower the impedance. Thus, if the r.f. source behaved as a constant voltage source, power delivery would be inversely proportional to tissue thickness. However, thinner tissue requires less energy to coagulate than thick. For example, if the tissue is half as thick, half the energy is required, yet power delivery will be doubled. With a constant r.f. voltage supply it is, therefore, desirable, to vary the duty cycle to reduce variation in the speed of clinical effect, the speed of effect being proportional to the square of thickness. It is possible that a particular instrument may be used over a 5 to 1 range of tissue thickness. Speed of effect variation would be 25 to 1. The strategy of constant voltage and variable duty cycle is not, therefore, preferred. The need to overcome current hogging in thin tissue is greater than in thick tissue for the reasons outlined earlier. It has been found that a peak power of 200W is more than sufficient to achieve sub-surface vapour with the largest of instruments and the thinnest tissue. Limiting the power requirement rather than burst duration is advantageous in terms of instrument compatibility, reducing the variation in treatment time and placing less demand on the r.f. generator. Changing burst duration whilst maintaining a constant r.f. voltage yields different treatment rates for different thicknesses.

The worst case for inducing sticking is when the tissue is thin due to the lack of current sharing, and this is often compounded by the requirements of the instrument design. As far as a single r.f. burst is concerned, sufficient energy is supplied to create multiple vapour pockets. The energy requirement of the burst is determined by the volume of tissue grasped, and hence the dimensions of the forceps jaws. Over a wide range of instrument configurations, the energy requirement to reach 100° C. may lie in the range of 2 to 20J. Minimum burst width at 200W is, therefore, between 10 ms and 100 ms respectively. The latent heat of vaporisation defines a corresponding energy requirement of 20 to 200J. This suggests that, if the burst is set to 200W for 100 ms, there would be sufficient energy to vaporise the total electrolytes of the minimum tissue volume grasped. In practice, the sub-surface creation of vapour causes a dramatic increase in impedance. The vapour formation and the above-mentioned voltage clamping create an automatic regulating effect so that energy delivery beyond that needed to cause hot spots is limited. As the energy required for complete vaporisation is ten times greater, there is a large operating window of available settings. It is, therefore, possible to operate with a potential 20J of energy per burst. However, it is not necessary for this first burst to create vapour when the tissue is thick. The creation of vapour within thicker tissue has a higher potential risk of popping. The auto-regulation of the maximum voltage clamp reduces the burst energy into the higher impedances created by thicker tissue. Lower burst energy can, therefore, be used than that indicated in the earlier analysis, and yet still achieve the tissue effect. The auto-regulating effect is a function of the power delivery. The lower the burst power for a given energy, the less pronounced this effect.

The subsequent "off"-time allows condensation and thermal relaxation. This is a comparatively slow process. The hot vapour condenses relatively quickly, but the subsequent thermal conduction is slow. Using forceps of low thermal mass and thermal conductivity, it has been found that periods in excess of 100 ms are required before sufficient thermal relaxation can take place. Values in the range of 300 ms to 1 s are preferred. This thermal relaxation is important to ensure that the subsequent r.f. burst creates hot spots in previously untreated areas of the tissue. The "on" time of each burst is typically in the region of from 100 to 500 ms. These figures apply to power, voltage or current waveforms, as do the mark-to-space ratio and duty cycle figures referred to in this specification.

The cycle of burst and relaxation times is continued until the tissue contained within the grasp of the forceps is completely treated. Due to the higher thermal capacity of thicker tissue, vapour may not be generated in the first burst, but only in subsequent bursts. Electrical evidence of vapour generation is provided in the current and voltage traces monitored during each power burst. When vapour is created, the voltage clamp is reached and current decays. The next burst produces a higher initial current as a result of the condensation during the "off"-time. This initial current is usually 50% greater than the end current of the preceding burst. The auto-regulating effect of vapour creation, in conjunction with voltage clamping, prevents complete desiccation. The current during each burst exhibits a decay similar to an exponential decay with the average value for each burst decreasing in a similar fashion. Vessel sealing occurs when the average delivered current decays to approximately 30% or less of its peak value. The most notable feature about the completion point is that the outer surfaces of the treated tissue in contact with the electrodes 11, 12 are still moist. The fact that this moisture is not vaporised helps prevent the extension of thermal damage beyond the treatment site which would otherwise occur as a result of surface steam condensing on adjacent tissue. The moisture also prevents tissue sticking, and the uniformity of treatment enables a more reliable determination of a coagulation end-point without the necessity of surface desiccation inherent in conventional systems.

Figure 5:
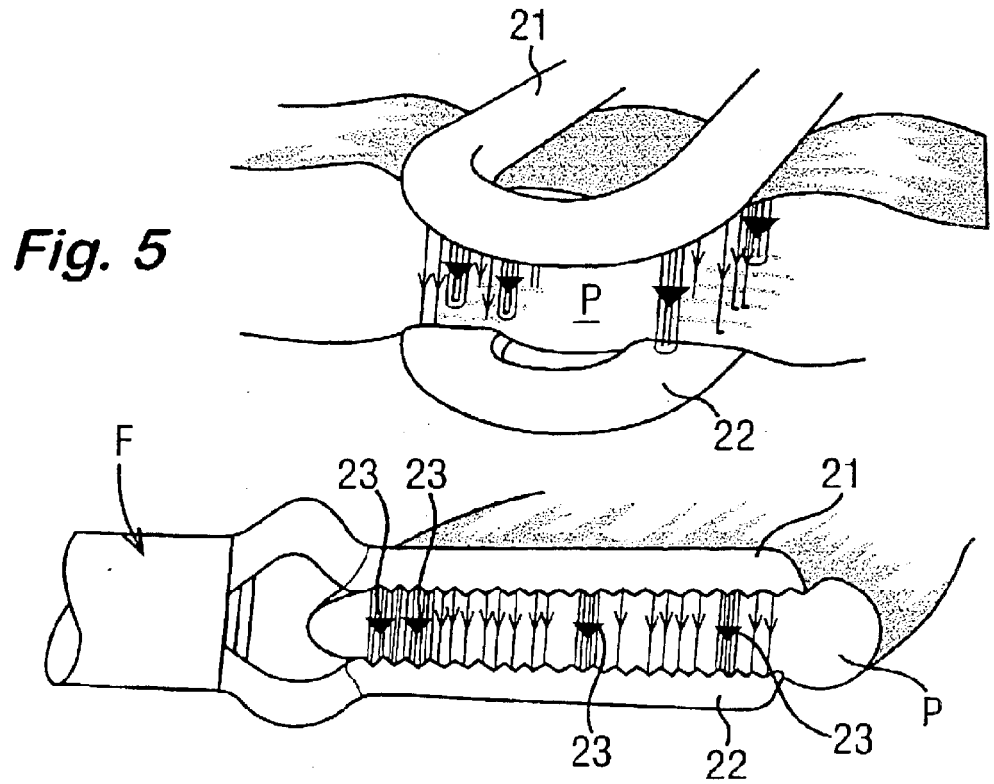
FIGS. 5–11 contrast the effect obtained on a tissue pedicle using forceps operated conventionally and as part of a system in accordance with the invention.

FIGS. 5 to 11 illustrate the use of BiCOAG Cutting Forceps F operated conventionally and as part of a system in accordance with the invention. Each of these figures shows two perspective views of the forceps F, respectively from the distal end thereof and from the side. Thus, FIG. 5 shows a tissue pedicle P grasped in the jaws 21, 22 of the forceps F, the forceps being operated in a conventional manner. The current density between the forceps jaws (electrodes) 21, 22 is variable over the tissue contact area creating zones of high current density, shown by the arrowhead symbols 23 in FIG. 5. The variations in impedances which may occur as a result of, amongst other things, the non-parallel closure of the forceps F creates the zones 23 of high current density. The zones 23 of high current density create hot spots at the contact surfaces between the tissue and the forceps jaws 21, 22. The hot spots created in the zones 23 of high current density reduce the impedance of these zones even further compared to the other areas of the tissue. All the current from the output becomes concentrated in these hot spots which exhibit the phenomenon of current hogging. The hot spots become even hotter until the tissue on the surface becomes completely desiccated and the impedance falls. Only then will the areas of untreated tissue then be treated. This is well demonstrated when the proximal end of the forceps jaws are more closely opposed than the tips, in that the effect is seen to move along the length of the jaws during application. Current hogging produces two undesirable effects: the tissue surface must be desiccated to ensure complete treatment which increases the risk of tissue sticking, and the application time must be prolonged to ensure complete treatment which increases the collateral margin.

The generator and system described in this specification overcome these problems in the following ways. The zones of high current density are instantly created, as shown in FIG. 1, by the burst of bipolar r.f. energy. As has already been described, these zones of higher current density are more likely to be created in thinner tissue when the forceps jaws are more closer together. This situation can be created by first grasping the tissue within the jaws, and preferably employ a ratchet feature on the BiCOAG Cutting Forceps so that the tissue is crushed and held at an optimal cross-section. Under these circumstances, when the first pulse is applied, the tissue in the zones of high current density reaches 100° C. virtually instantly.

Figure 6:
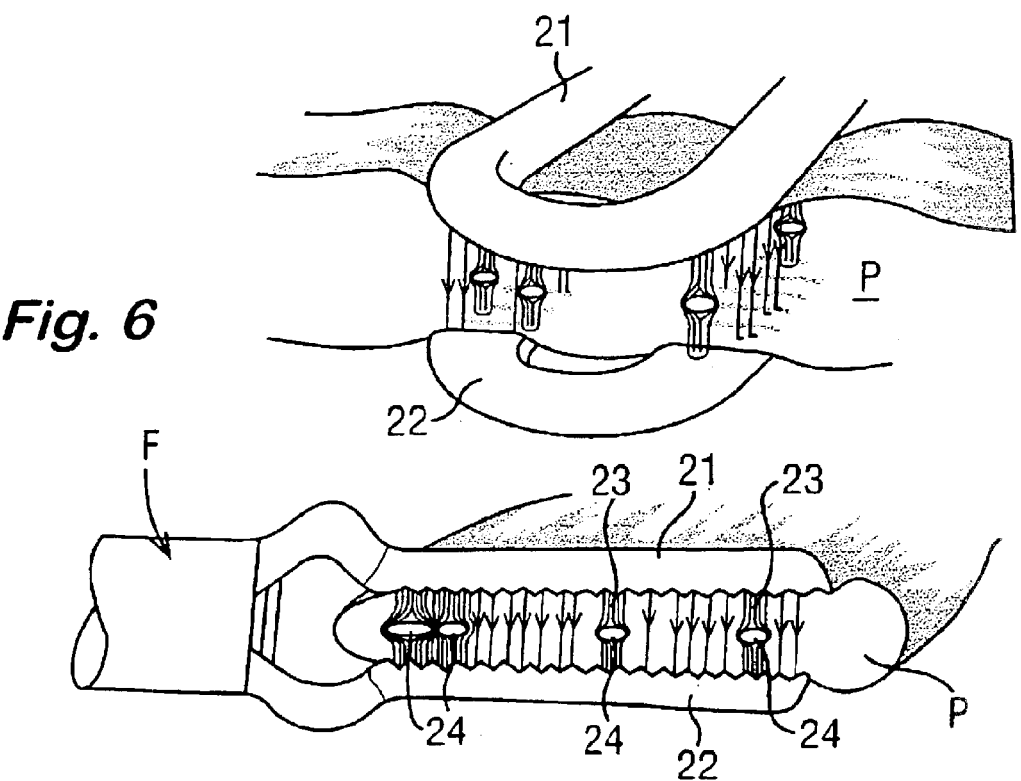

FIGS. 6 to 11 show the use of the forceps F when operated as part of a system in accordance with the invention, that is to say the forceps F are supplied with electrosurgical energy by an r.f. generator as described in this specification. Thus, as shown in FIG. 6, the power of the first pulse is dissipated in the centre of the tissue pedicle P in zones 23 of high current density, creating pockets 24 of water vapour (steam) in the intracellular and interstitial fluids. High current and high power are used to form the vapour pockets 24.

Figure 7:
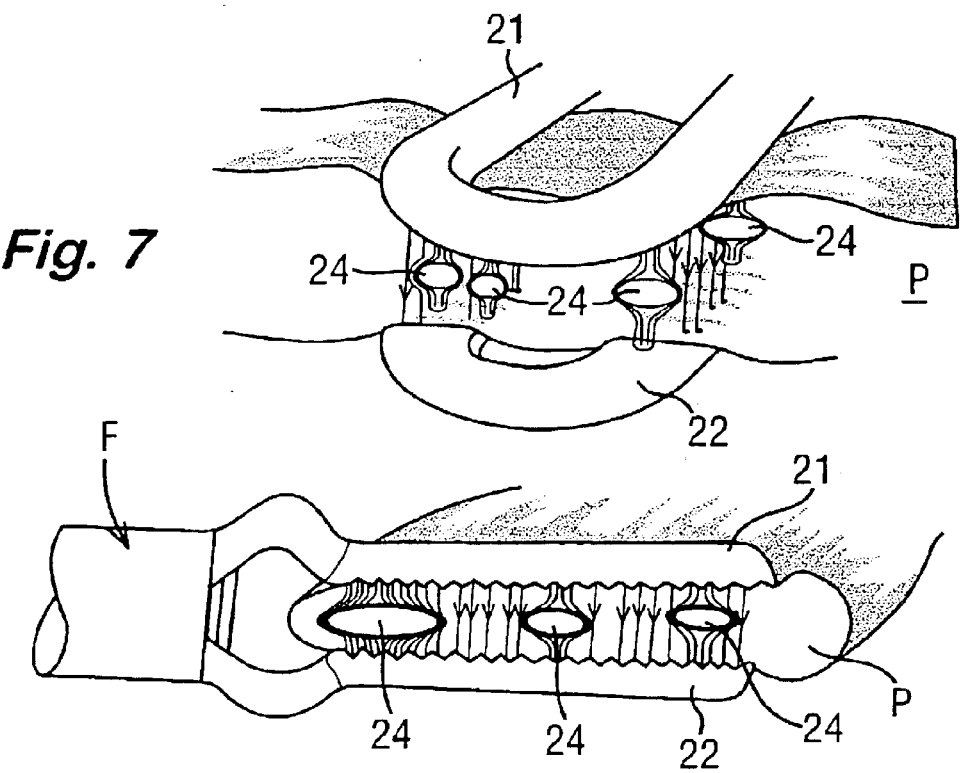

Such power and current levels are not normally available from a conventional bipolar electrosurgical generator for "dry field" electrosurgery. The creation of the vapour pockets 24 produce two benefits: the vapour pockets 24 produce a high impedance barrier which prevents further current hogging, and the highest current densities occur around the lateral edges of the vapour pockets, as shown in FIG. 7. Heat generation and coagulation start internally, within the tissue pedicle P, rather than in the external contact area between the tissue and the forceps jaws 21, 22.

Figure 8:
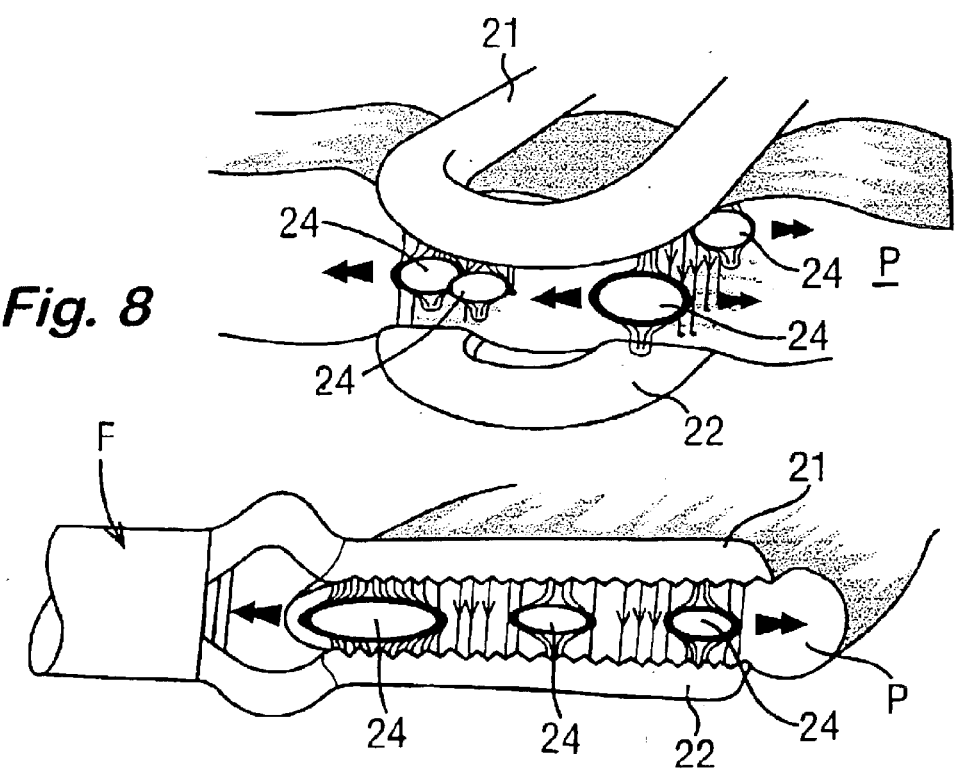

Referring now to FIG. 8, the pathway of least resistance for the current flow is around the vapour pockets 24. This concentration of current expands the vapour pockets 24 at their lateral edges where the highest temperatures occur. The tissue effect, therefore, naturally moves to untreated areas within the pedicle P. During use, the tissue is seen to swell with each energy pulse. If, however, the vapour were to persist in growing, less and less tissue would be conducting the current. This would generate vapour far more quickly, so that a potential runaway situation could occur, producing the bursting or popping associated with prolonged application from a conventional generator. The auto-regulating feature of the present system shuts off the power of a given energy pulse in microseconds when excessive vapour formation occurs. Excessive vapour formation is further avoided by the termination of the energy pulses in accordance with the cycle of burst and relaxation times mentioned above.

Figure 9:
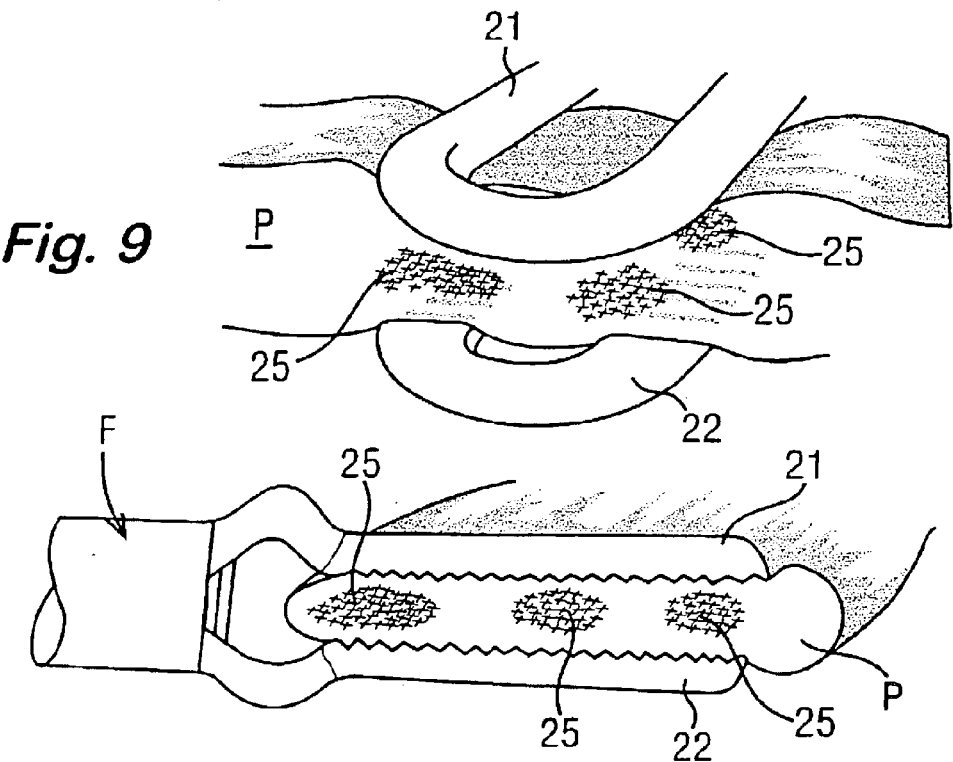
Figure 10:
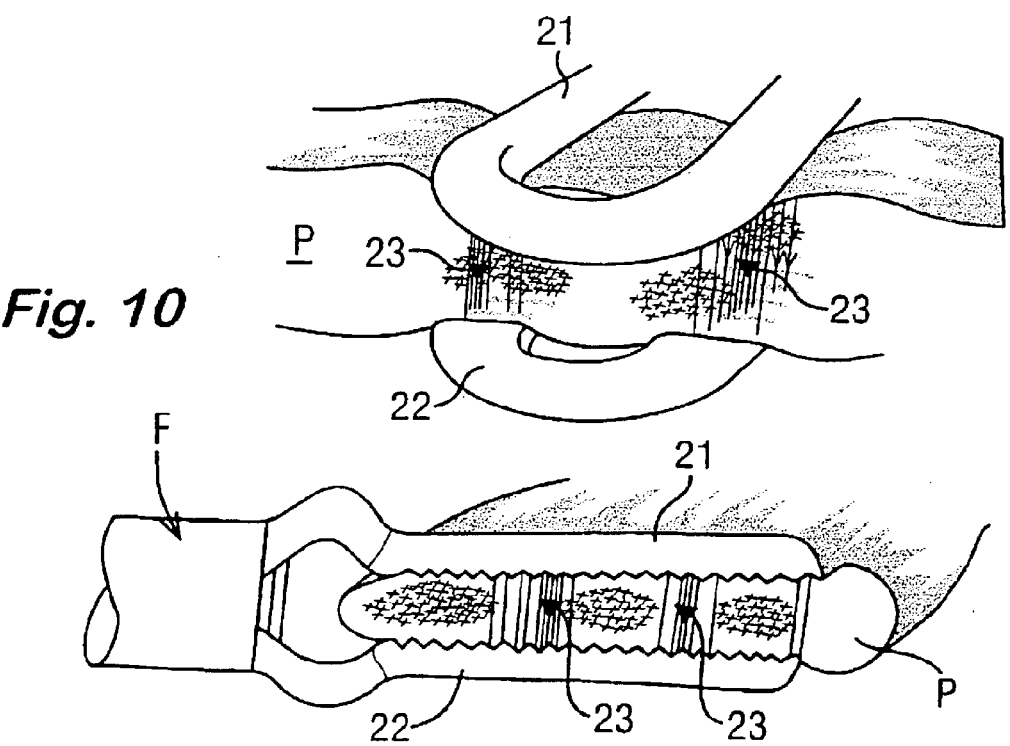

Referring now to FIG. 9, when the first energy pulse is terminated, the vapour pockets 24 collapse, leaving areas 25 of desiccation inside the tissue pedicle P but none on the surfaces between the forceps jaws 21, 22 and the pedicle, which surfaces remain moist. Heat generated within the tissue pedicle P dissipates in the colder areas of the pedicle as the vapour condenses. Once this thermal relaxation has been allowed to occur, a second energy pulse is applied as shown in FIG. 10. The zones 23 of high current density are now created in previously untreated areas, because of the higher impedance of the desiccated tissue produced by the first energy pulse. Vapour pockets 24 (not shown in FIG. 10) once again form in these zones, and expand laterally to include any untreated areas.

Figure 11:
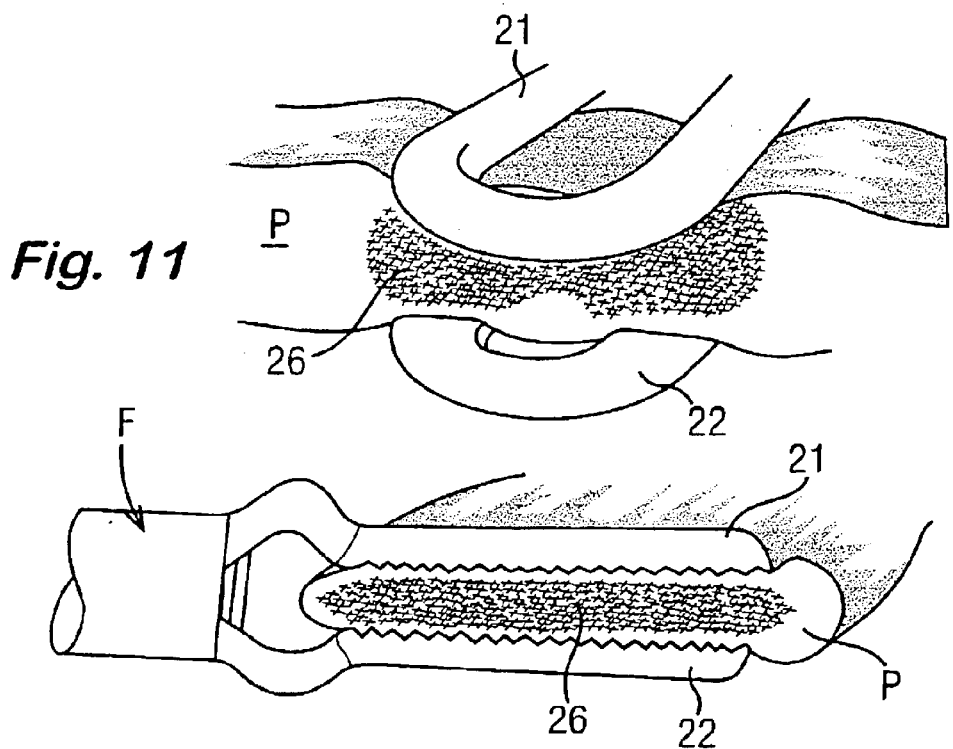

The on-off cycle of bipolar r.f energy pulses is continued until the power absorption at each pulse falls below a level indicative of complete coagulation, as indicated by the reference numeral 26 in FIG. 11. This point corresponds to the point at which no more zones of high current density can be created. This gives an automatic indication when the tissue within the pedicle P is uniformly treated with surface coagulation, but not desiccated. The maximum effect is produced within the tissue pedicle P with the surfaces adjacent to the jaws 21, 22 remaining moist and non-adherent to the jaws.

The measures described above provide for faster uniform coagulation of vascular pedicles without the need to skeletonise. Skeletonisation is a surgical technique in which the fat and connective tissue which normally surrounds vessels is removed to expose the vessels themselves. This removes what, in effect, is a high impedance barrier to the transfer of bipolar r.f. energy to the lower impedance vascular structures within a pedicle. The advantage of the present system in this situation is provided by the preferential absorption of energy within a pedicle.

Figure 12:
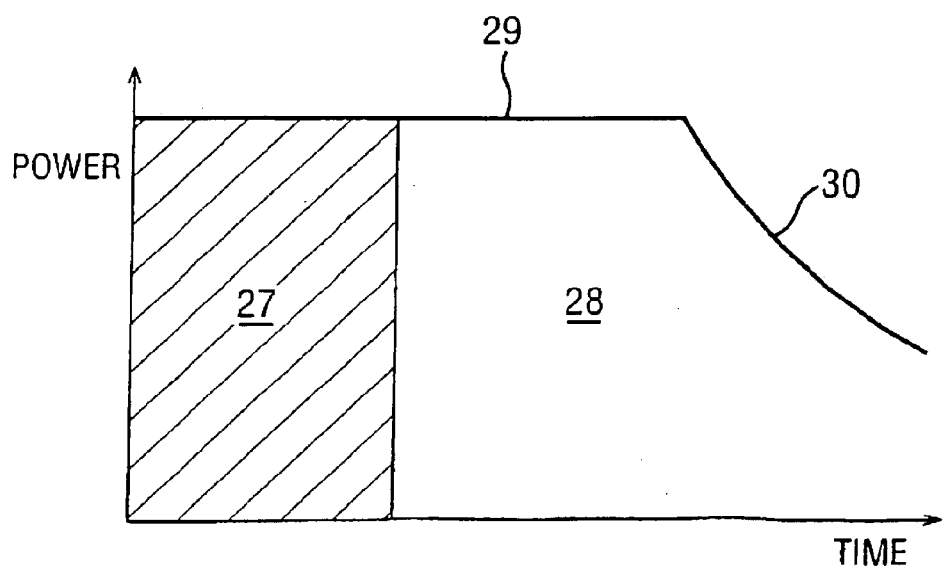
FIGS. 12 and 13 are graphs illustrating the comparative efficiency of energy delivery using forceps operated conventionally and as part of a first system in accordance with the invention.

During practical use of the system, a surgeon will need to deliver less energy to achieve a therapeutic effect than if a conventional, continuous, bipolar r.f. output was used. The graph of FIG. 12 illustrates the therapeutic effect on tissue after delivery of a certain amount of energy over a certain amount of time delivered from a continuous output bipolar r.f. source. During an initial phase 27 of a treatment cycle, energy delivery is effective. As current hogging occurs, some tissue areas reach the therapeutic level before others. To create haemostasis, all tissue areas need to achieve this level. To ensure that these other regions are brought to the therapeutic temperature, power has to be applied for a longer period of time. During this extension period 28 of the treatment cycle, most of the applied energy is wasted in boiling the electrolytes in the region that initially formed the current hogging point. The appropriate treatment time is often so indeterminate that power is applied until complete desiccation occurs. Boiling occurs while power is maintained at a preset level 29. Once desiccation occurs, the load impedance rises and the delivered power decreases, as shown by the decay part 30 of the curve in FIG. 12. This excessive boiling of electrolytes helps explain tissue sticking, charring and lateral thermal margins.

Figure 13:
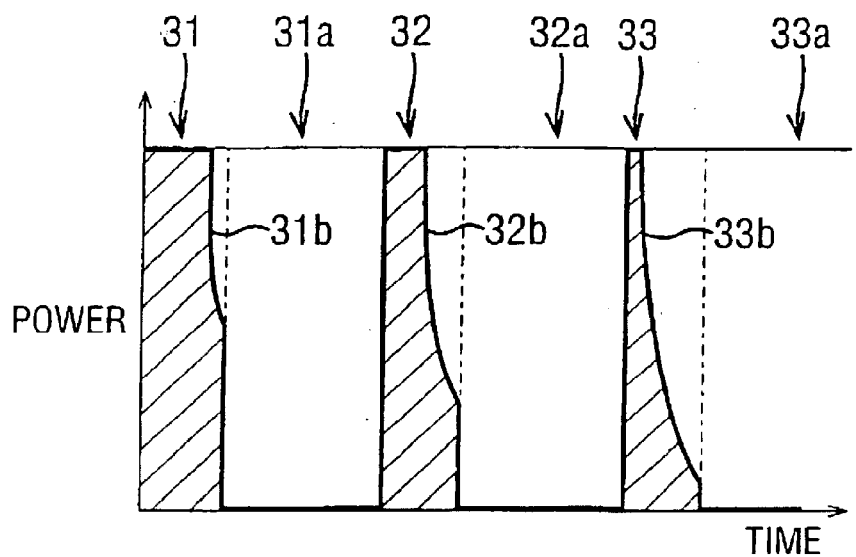

The graph of FIG. 13 illustrates how a desired therapeutic effect can be reached using the present system after three r.f. pulses 31, 32 and 33 are applied. Each pulse 31, 32, 33 is followed by a respective 'relaxation period' 31*a*, 32*a*, 33*a*. The first pulse 31 that is applied is capable of creating vapour. As this vapour forms internally, it interferes with power delivery, causing a reduction in power (indicated by the line 31*b*) towards the end of the pulse. The energy absorbed by vaporising the small quantity of electrolyte involved is then redistributed during the 'relaxation period' 31*a* before the next pulse 32 of energy is delivered. This redistribution occurs by condensation. The amount of vapour produced by each subsequent pulse is greater, and so results in even further power reductions, but also an even greater dispersion of energy throughout the tissue. This redistribution of energy by the condensing vapour is demonstrated by the fact that the initial energy delivery for each pulse is not interrupted by vapour. The energy of each pulse, as represented by the shading in FIG. 13 is almost entirely effective. As little or no excess energy is used, and the heating occurs from inside to outside (unless the surgeon chooses otherwise, e.g. when a thermal treatment margin is required), there will be little excess thermal energy to cause sticking, charring or collateral tissue damage. The graphs of FIGS. 12 and 13 can be obtained by application of a pair of forceps to morbid vascular tissue and energising continuously or in pulses respectively.

Figure 14:
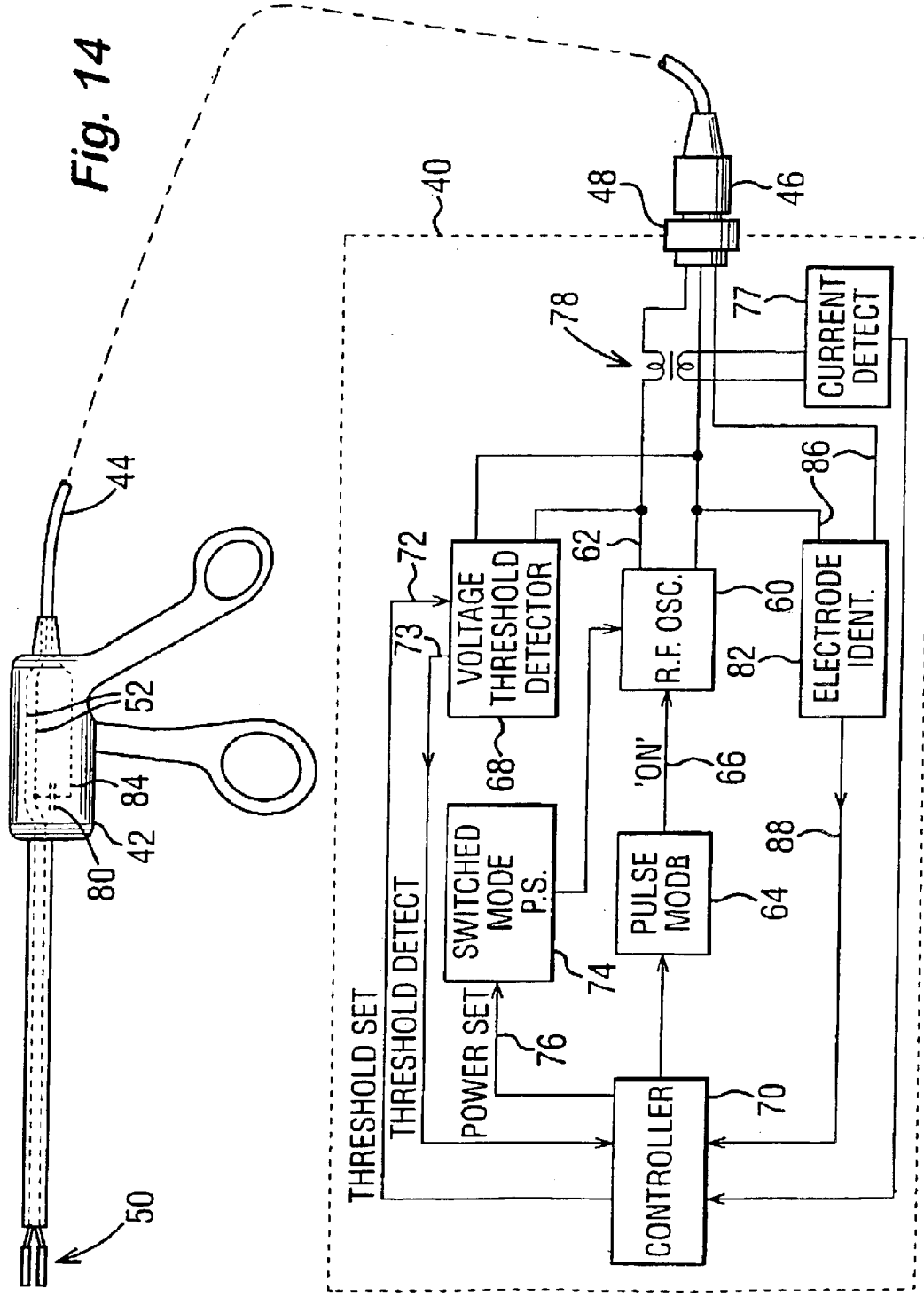
FIG. 14 is a diagrammatic representation of a system in accordance with the invention, comprising an electrosurgical generator and an instrument in the form of a pair of forceps.

Referring to FIG. 14, an electrosurgical system in accordance with the invention comprises a generator 40 for generating radio frequency power, and an electrosurgical instrument comprising the assembly of a handheld forceps unit 42, a connecting cable 44, and a connector 46 for removably connecting the assembly to the generator 40 via a generator connector 48 containing the generator output terminals. Instead of being on the generator, the connection interface between the forceps unit 42 and the generator 40 may be on the forceps unit 42 itself, the significant point being that alternative treatment units, whether forceps or otherwise, may be connected to the generator 40.

The forceps unit 42 has a pair of electrodes 50 which are coupled via power delivery conductors 52 passing through the body of the forceps unit 42 and the cable 44 to the connector 46 where they are connected to two of the output terminals (not specifically shown) of the generator in generator connector 48, to allow supply of radio frequency power from the generator to the electrodes. Radio frequency power for supply to the electrodes 50 is generated in an r.f output stage 60 having output lines 62 associated with respective output terminals in the generator connector 48. As described above, the generator 40 is arranged to supply 100% amplitude-modulated radio frequency power with a carrier frequency in the range of from 100 kHz to 500 kHz and with a pulse repetition rate in the region of 0.7 to 3 Hz, typically. The modulating waveform is fed to the r.f. output stage 60 by a pulse modulator 64 via connection 66.

The peak r.f. voltage generated between the output stage output lines 62 is limited, typically to 200V peak, by the combination of a voltage threshold detector 68, coupled between the lines 62, and a controller stage 70. When the voltage threshold, set by the controller via threshold set line 72, detects a peak output voltage exceeding the set threshold voltage, a threshold detect signal is fed to the controller 70 via the detector output line 73 and the r.f power is reduced by adjusting a switched mode power supply 74 which supplies power to the output stage 60, the controller signal being applied via power set line 76.

Another function of the controller 70 is to set the frequency and pulse width or mark-to-space ratio of the pulse modulation applied to the r.f. output stage 60 by the pulse modulator 64.

The controller 70 also receives an output current detection signal from a current detector circuit 77 coupled in one of the output lines 62 by a current transformer 78.

It will be appreciated that when, during use of the system, the surgeon wishes to coagulate, for instance, a pedicle, between the electrodes 50 of the forceps unit 42, he operates the forceps to grasp the pedicle between the electrodes 50 and activates the generator 40 by means of a foot switch (not shown), whereupon the r.f. output stage 60 is activated by the pulse modulator 64 so that a 100% amplitude-modulated r.f. signal is fed to the electrodes 50 at a frequency set by the controller 70, the mark-to-space ratio being such that the "off"-time of the output stage 60, as determined by the controller 70 and the pulse modulator 64, is at least. 100 ms between each successive pulse. With successive pulses, the instantaneous applied power decays towards the end of each pulse as vapour is formed within the tissue. As described above, the "off"-times 31*a*, 32*a*, 33*a* (FIG. 13) are each sufficient to allow the vapour within the tissue to condense before application of the next pulse, but in each successive pulse, if the applied power level is held constant, the power decays to a finishing value lower than that occurring in the previous pulse. In the present embodiment, this decay is sensed by the current detector circuit 77 and the controller 70, and the controller is arranged to terminate the pulses when the rms current at the end of one of the pulses falls below a predetermined fraction of the rms current at the beginning of the pulse. In this case, the pulses are cut off when the finishing current is 30% or less than the starting current. Accordingly, in this embodiment, a current threshold is used to terminate a sequence of pulses, i.e. termination occurs when the r.f. current falls below a predetermined current threshold. As an alternative, the sensing circuitry of the generator 40 may be arranged to deliver a sensing signal to the controller which is proportional to power, so that treatment can be terminated when the instantaneous power falls below a predetermined power threshold. Variations on this principle may be used, including current or power thresholds which are absolute, or which are specified as a fraction of a value at the commencement of treatment, or as a fraction of the value at the commencement of the pulse in question.

Figure 15:
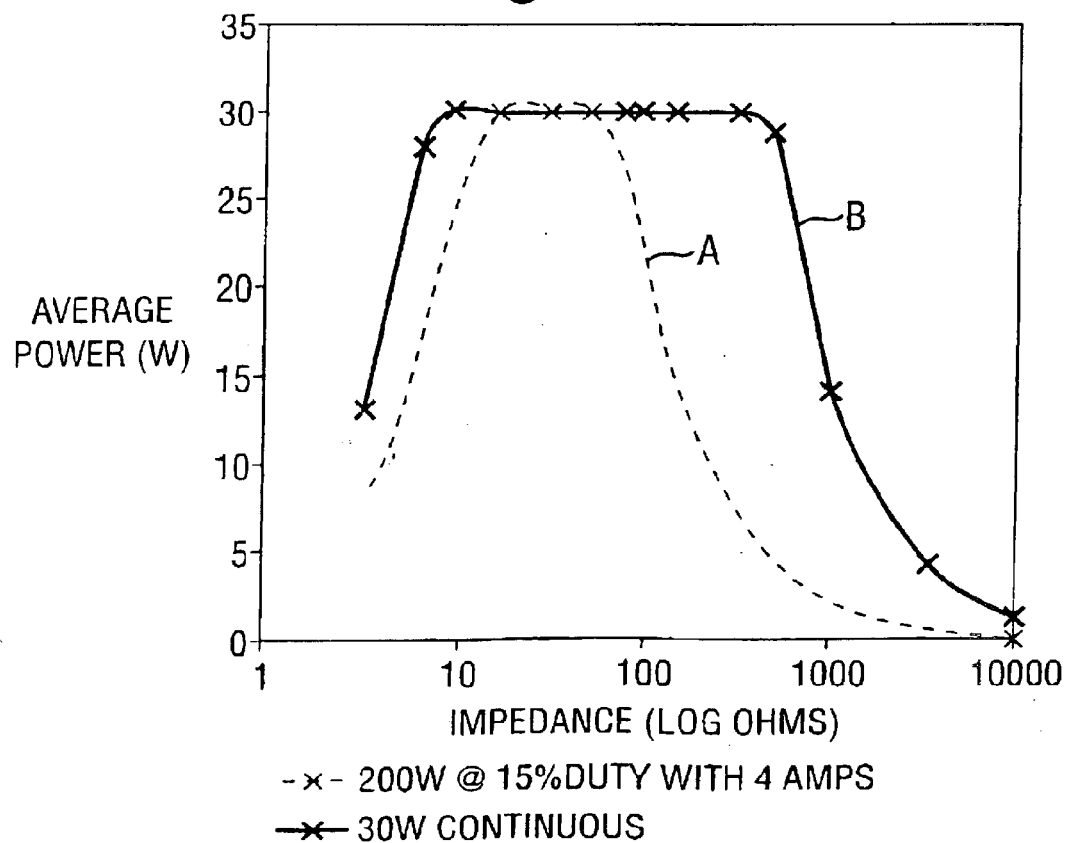
FIG. 15 is a graph showing the average output power of an electrosurgical generator as a function of load resistance, when operated in a continuous mode and in a pulsed mode with a 15% pulse duty cycle.

At this point it is worth noting that the combination of the pulsed output and a voltage limit (typically 120V rms) create a power versus impedance load curve (averaged over the pulses) which is somewhat narrower than that of conventional generator operating with a continuous output. This is illustrated in FIG. 15. The present generator may typically produce an instantaneous power output of 200W when running at a 15% duty cycle, the current being limited to a value in the region of 1 amp to 5 amps rms, which yields a power peak between 10 ohms and 100 ohms load impedance, in contrast to a conventional generator operating at an average power of, typically, 30 watts which would produce an approximately flat power-versus-load impedance curve in which power is maintained at or near a maximum value over a ten-fold range of impedance, e.g. from 10 ohms to well in excess of 100 ohms. In FIG. 15, the dotted curve A corresponds to a 15% duty cycle pulsed output with a peak power output of 200W and a current rating of 4 amps r.m.s. The solid curve B represents the power-versus-impedance characteristic for the conventional generator operating with continuous r.f. output of 30W. Both curves are voltage-limited at 120V r.m.s. It will be seen that although the pulsed generator delivers its maximum power over a narrower impedance range than the continuously operating generator, nevertheless maximum power is delivered over a load impedance range starting at no more than 20 ohms. A realistic lower limit for peak power delivery is 100W when driving loads down to 20 ohms, recognising that the maximum impedance into which this peak power can be delivered can be delivered is determined by the voltage limit (here 120V r.m.s) imposed to prevent arcing. The limitation in load curve width is desirable inasmuch as it provides the auto regulation feature described above at the end of the treatment. The extent to which power can be delivered into a low load impedance is governed by the current rating of the generator. In the present generator, an rms current value in excess of 1.5 amps at the start of each pulse is typically achieved, with 3 or 4 amps being attainable. It will be appreciated that if the electrodes 50 of the forceps unit 42 are comparatively large in their tissue contact area, the load impedance presented to the generator will be comparatively low. The load impedance also decreases as the thickness of tissue grasped between the electrodes 50 decreases. It is possible to improve the speed of treatment by altering the pulses produced by the generator according to the characteristics of the instrument to which it is connected. Although large area electrode produce a low load impedance, the thermal relaxation time of the larger area of tissue grasped is longer due to the longer thermal conduction paths. Smaller area electrodes can be treated with a larger duty cycle or mark-to-space ratio, due to the lower thermal relaxation times, and with lower peak power. Larger duty cycles have the effect of increasing the ability of the generator to match into high impedance loads (due to the power-versus-load peak extending to higher impedance values). Consequently, increasing the duty cycle when the electrodes are small in area provides the advantage of faster treatment.

Changing the pulse duty cycle, then, in conjunction with the upper voltage clamp has the effect of changing the load curve to suit the instrument being used. Referring again to FIG. 14, pre-adjustment of the pulse characteristics may be performed by arranging for the instruments which are to be connected to the generator 40, such as forceps unit 42, to have an identification element 80 which may be sensed by a sensing circuit 82 in the generator when the instrument is connected to the generator output connector 48. In the example shown in FIG. 14, the identification element 80 is a capacitor of a specific value coupled between one of the power leads 52 and a third lead 84 in the cable. These same two leads are coupled via the connectors 46, 48 to a pair of inputs 86 of the sensing circuit 82, which acts as an electrode identifying circuit by responding to the value of the capacitor. The controller 70 varies the basic or initial pulse duty cycle according to an identification signal received from the identification circuit 82 via line 88. Details of the electrode identification circuit 82 and its interaction with the identifying element 80 are described in European Patent Publication 0869742A, the contents of which are incorporated herein by reference.

Accordingly, by arranging for different value capacitors 80 to be incorporated in different instruments according to, for instance, electrode tissue contact area and other properties of the instrument affecting load impedance and thermal relaxation time, the generator can be automatically configured to produce a pulsed output particularly suited to the instrument in question. In particular, as instruments with larger tissue contact areas are selected, the preset duty cycle or mark-to-space ratio is lowered and/or the pulse frequency is lowered.

The controller may alter not only the mark-to-space ratio, but also pulse frequency and power output via, in this case, the pulse modulator 64 and/or the switched mode power supply 76.

Figure 16:
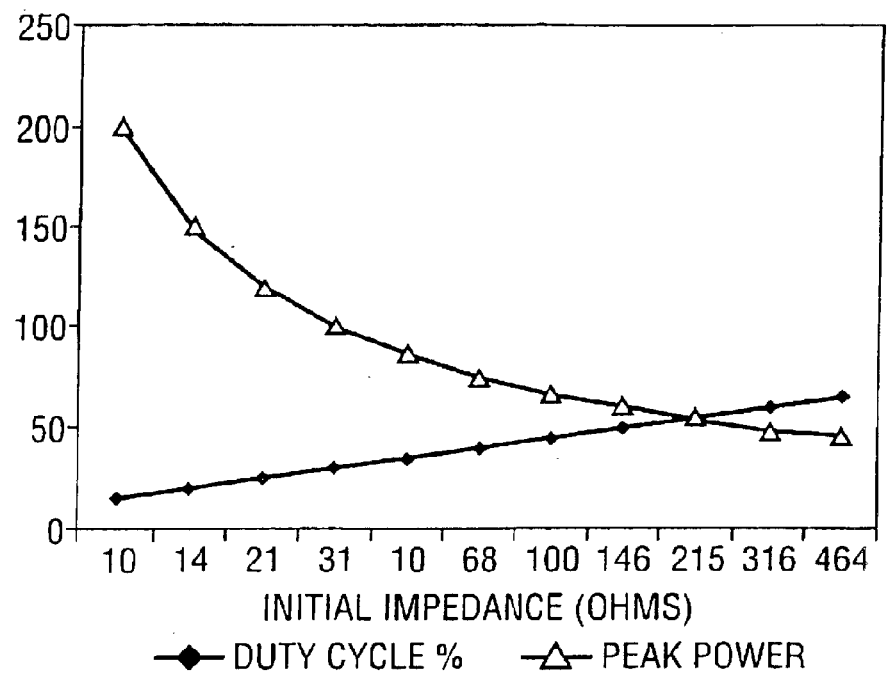
FIG. 16 is a graph showing the variation of pulse duty cycle and peak power according to initial load impedance in one embodiment of generator in accordance with the invention.
Figure 17:
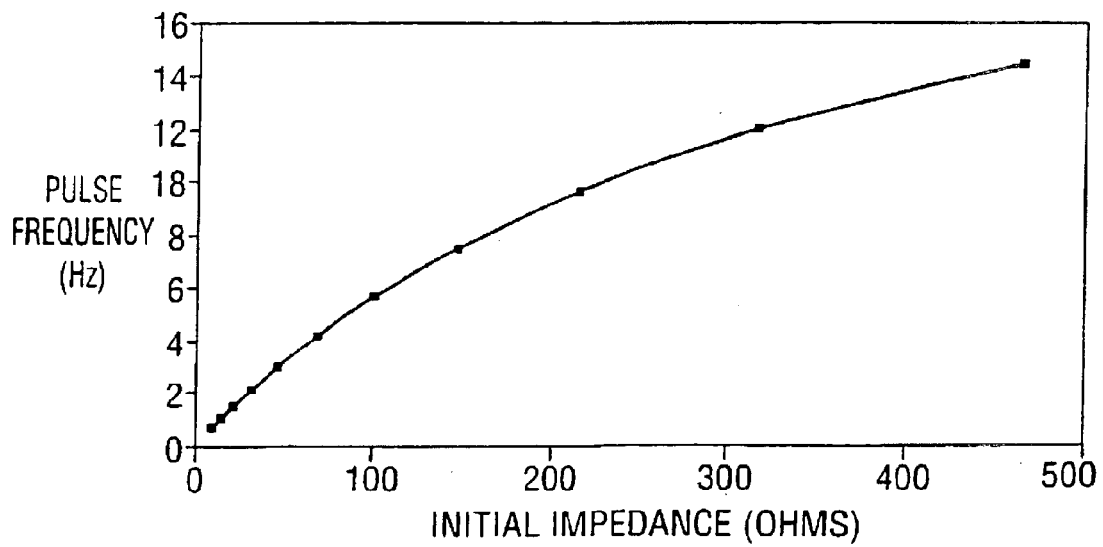
FIG. 17 is a graph showing the variation of pulse frequency with initial load impedance in the same generator.

As an alternative to identifying the instrument or instrument category, the generator 40 may be provided with a sensing circuit for sensing the load impedance across the output lines 62 of the output stage 60 at or around the instant at which the surgeon commences electrosurgical treatment, the pulse characteristics thereby set being maintained until treatment is finished. Referring to FIG. 15, the pulse duty cycle can be increased, as shown, with increased initial load impedance. In the example shown, the duty cycle is maintained below 50% (i.e. a mark-to-space ratio of 1:1) for impedances less than about 140 ohms. Referring to FIGS. 15 and 16 together, the controller may be arranged, in addition, to set the peak power (FIG. 15) and the pulse frequency (FIG. 16) concurrently according to the initial load impedance, the power being set higher and the pulse frequency being set lower for low initial impedances than for high initial impedances. The initial impedance may be sensed by monitoring the current, given that for a known initially applied power, the initial load impedance is inversely proportional to the square of the output current.

Further benefits can be obtained by arranging the generator so as to perform a treatment cycle consisting not merely of a plurality of pulses of a single preset duty cycle, but by dividing the treatment cycle into periods in which the generator output signal begins as a pulsed r.f. signal with a predetermined duty cycle and finishes with a different characteristic. Referring to the power-versus-time graph of FIG. 18, the treatment cycle may have an initial period 130 in which the r.f. power signal consists of a series of pulses 131, 132, 133 with a predetermined duty cycle, followed directly by a subsequent period 140 in which the r.f. power signal is a c.w. signal 141 of much lower power amplitude. Typically, during the initial period 130, the pulses 131 to 133 have a duty cycle in the region of from 15% to 30% with a peak power of 200W. The transition from the initial period 130 to the subsequent period 140 may be controlled by feedback from the output circuitry of the generator. Referring back to FIG. 14, the switched mode power supply 74 is controlled via line 76 by the controller 70 which is, in turn, responsive to a sensing signal on line 73 from the output voltage threshold detector 68. Being a switched mode device, the power supply 74 has its own switching frequency which, in this embodiment, may be in the region of 25 kHz, supplied as a pulse stream from the controller 70. In this example, the r.f. output voltage of the generator 40 is limited by interrupting the switching pulses supplied to the power supply 74 when the output voltage exceeds a predetermined threshold (typically 120V r.m.s., as mentioned above). By monitoring the power supply switching pulses generated by the controller 70, it is possible to determine the amount of energy delivered by the generator. Counting the switching pulses, therefore, offers a convenient way of monitoring electrical conditions at the generator output. In particular, referring to FIG. 18, the decrease in delivered power due to the formation of vapour in the tissue and visible as decay curves 132b and 133b in the power waveform, is the result of interruptions in the power supply switching pulses produced in response to the output voltage having exceeded the threshold set in the voltage threshold detector 68 (FIG. 14). Accordingly, by counting the power supply switching pulses, it is possible to determine when the low duty cycle waveform ceases to be advantageous, whereupon the controller 70 can adjust its output to cause the switched mode power supply to deliver energy on a continuous or more nearly continuous basis, but at a significantly lower peak power level, as illustrated by the c.w. waveform 141 in FIG. 18. Typically, the average power delivered during this subsequent period 140 of the treatment cycle is the same as the average power delivered during the initial period 130.

The more nearly continuous power delivery may be obtained, instead, by arranging for the r.f. power signal during the subsequent period to take the form of a pulsed signal with a significantly higher duty cycle but lower peak power, as shown in FIG. 19. In this embodiment, the controller 70 is arranged such that, as before, the initial period 130 of the treatment cycle consists of a plurality of pulses 131, 132, 133 with a low duty cycle and high peak power. Again, the transition to the subsequent period 140 is carried in response to electrical conditions at the generator output. In the subsequent period 140, however, the duty cycle is higher, e.g. at least twice that of the initial period, and the peak power is correspondingly reduced to result in at least approximately the same average power. Further vapour formation may occur in the tissue during the subsequent treatment cycle period 140 resulting in operation of the voltage clamp in the same way as during the initial period, as evident from the decay portion 143b of pulse 143.

In an alternative embodiment, not shown in the drawings, the treatment cycle may have more than two periods in which the r.f. power signal has different characteristics. In particular, the signal may consist of a succession of pulses beginning with a first group of pulses having a first low duty cycle, followed by a second group of pulses having a second greater duty cycle, followed by a third group of pulses with a third, yet greater duty cycle, and so on, so as to maintain optimum coagulation effectiveness as the tissue characteristics change. In other words, a three stage treatment cycle may be employed, each stage consisting of a number of pulses with its own respective fixed duty cycle. Typically, the successive stages have pulses with duty cycles of 15%, 30%, and 60%, and peak power values of 200W, 100W and 50W respectively, in order to maintain an approximately constant average power delivery.

The effect common to all three alternatives described above is that the load curve of the generator has an initially narrow characteristic as exemplified by curve A in FIG. 15, but is extended in the high impedance range as energy delivery becomes more nearly continuous, whether in the form of a c.w. output 141 as in FIG. 18, or in the form of an output with a higher duty cycle, as in FIG. 19. It follows that coagulation of the tissue being treated proceeds more quickly since power delivery into the tissue is maintained as the tissue impedance increases owing to vapour formation and, subsequently, localised coagulation of tissue.

Referring back to FIG. 13, it will be recalled that the "off"-times 31a, 32a, 33a are each sufficient to allow the vapour within the tissue to condense before application of the next pulse, but in each successive pulse, if the applied power level is held constant the power decays to a finishing value lower than that occurring in the previous pulse. Referring again to FIG. 14, this decay can be sensed by the current detector circuit 77 and the controller 70, and in a further embodiment of the invention the controller is arranged to reduce the applied power amplitude and increase the width of any given pulse in the succession of pulses when the rms current at the end of the preceding pulse falls below a predetermined fraction of the rms current at the beginning of that preceding pulse. For instance, the pulse width may be increased and the power amplitude decreased when the finishing current is 30% or less than the starting current. Accordingly, in this embodiment, a current threshold is used to control a progressive increase in pulse width and mark-to-space ratio and a progressive decrease in pulse amplitude.

In this preferred embodiment, the pulse power amplitude of the succession of pulses is progressively decreased and the pulse width progressively increased according to the time taken from the pulse rising edge to the instant at which the voltage threshold is reached, it being understood that the instantaneous power decay at the end of each pulse shown in FIG. 13 represents a constant voltage portion of the pulse, the voltage threshold imposed by the threshold detector 68 of FIG. 14 having been reached. Accordingly, by setting a time threshold for the initial portion of the pulse, i.e. the time delay to reach the voltage threshold, it is possible to cause the next pulse to be reduced in power amplitude and increased in width when the time delay is less than the time threshold. Variations on this principle are possible. For example, the degree to which the time delay is less than the time threshold may be used to control the degree to which the next pulse is reduced in amplitude and increased in width. Alternatively, the fraction of the respective pulse width which elapses before the voltage threshold is reached may be used to control the succeeding pulse amplitude and width, rather than having a fixed time threshold.

In another preferred embodiment, the sensing circuitry of the generator 40 may be arranged to deliver a sensing signal to the controller which is proportional to load resistance, so that pulse amplitude can be decreased and pulse width can be increased as the load resistance rises. Variations on this principle may be used, including current or load impedance thresholds which are absolute, or which are specified as a fraction of a value at the commencement of treatment, or as a fraction of the value at the commencement of the pulse in question.

The tailoring of the pulse width or duty cycle to smaller or larger area electrodes can be achieved at least to some extent automatically by controlling the change in pulse amplitude and width according to load resistance as set out above, but additional matching of pulse characteristics to instruments differing in this way can be obtained by setting the initial amplitude and width according to an identification element forming part of the instrument and sensed by the generator when the instrument is connected.

In particular, as instruments with larger tissue contact areas are selected, the starting duty cycle or mark-to-space ratio can be lowered and/or the pulse frequency lowered.

The effect of controlling pulse amplitude and pulse width in the ways described above is illustrated by way of example by the modulation waveform shown in FIG. 20. The generator output signal begins as a pulsed r.f. signal with a predetermined initial pulse width and duty cycle and finishes with a different characteristic, the pulses changing progressively in between. Thus, the treatment cycle may have an initial pulse 150 the width of which is between 15% and 30% of the pulse period. This is followed by pulses 151, 152, 153, 154 of progressively decreasing amplitude and increasing width as the impedance of the load increases. The initial pulse 150 typically has a peak power of 200W. The progressive change in amplitude and width may be controlled by feedback from the output circuitry of the generator. Referring back to FIG. 14, the switched mode power supply 74 is controlled via line 76 by the controller 70 which is, in turn, responsive to a sensing signal on line 73 from the output voltage threshold detector 68. Being a switched mode device, the power supply 74 has its own switching frequency which, in this embodiment, may be in the region of 25 kHz, supplied as a pulse stream from the controller 70. In this example, the r.f. output voltage of the generator 40 is limited by interrupting the switching pulses supplied to the power supply 74 when the output voltage exceeds a predetermined threshold (typically 120V r.m.s., as mentioned above). By monitoring the power supply switching pulses generated by the controller 70, it is possible to determine the amount of energy delivered by the generator. Counting the switching pulses, therefore, offers a convenient way of monitoring electrical conditions at the generator output. In particular, referring to FIG. 20, the decrease in delivered power due to the formation of vapour in the tissue and visible as decay curves 150b, 151b, and so on in the power waveform, is the result of interruptions in the power supply switching pulses produced in response to the output voltage having exceeded the threshold set in the voltage threshold detector 68 (FIG. 14). Accordingly, by counting the power supply switching pulses, it is possible to determine the rate at which the pulse amplitude should be decreased and pulse width increased, these changes in output being effected by the controller 70. Typically, the average power delivered during each pulse remains substantially constant over at least a major part of the treatment cycle from pulse 150 to the cessation of power application.

As mentioned above, the rate at which the pulses increase in width and decrease in amplitude can be determined, instead, by sensing load resistance. All in all, by arranging for the pulses to change progressively in this way, optimum coagulation effectiveness may be maintained as the tissue characteristics change. In other words, a continuously varying treatment cycle may be employed, consisting of a number of pulses each with its own respective width and amplitude. Typically, the pulse duty cycle increases from 15% to at least 60% and peak power values of 200W, down to 50W or less are used to maintain an approximately constant average power delivery.

Again, the effect of a modulation waveform such as that described above with reference to FIG. 20 is that the load curve of the generator has an initially narrow characteristic as exemplified by curve A in FIG. 15, but is extended in the high impedance range as energy delivery becomes more nearly continuous, whether finally in the form of a c.w. output, or in the form of an output with a higher duty cycle.

In another embodiment of the invention, the treatment cycle begins with at least one pulse of a predetermined ON-time (i.e. duration) followed by a predetermined OFF-time (i.e. duration of substantially zero power delivery). Thereafter, in a subsequent period of the treatment cycle, the r.f. power signal has a different characteristic, the transition from the initial period to the subsequent period being controlled by the control circuitry in response to the at least one monitored parameter. Preferably, the ON-time is less than or equal to 300 ms and the OFF-time is longer than the ON-time. As typical values, the ON-time is in the region of 100 ms and the OFF-time is about 700 ms. This implies a pulse repetition rate when plural pulses are delivered, in the region of 1 pulse per second. Alternative pulse repetition rates are possible, such that, for instance, the pulse repetition rate is 140 ms with the ON-time in the region of 400 ns and the OFF-time in the region of 100 ms.

The subsequent period of the treatment cycle may be characterised by a c.w. signal of a lower instantaneous power amplitude than the instantaneous power amplitude of the pulse or pulses of the initial period. Alternatively, the subsequent period may be characterised by a plurality of pulses of fixed or variable mark-to-space ratio and/or fixed or variable amplitude, the amplitude being different (preferably less than) the amplitude of the pulse or pulses of the initial period.

Preferably, the monitoring of an electrical parameter associated with the output terminals is performed during at least the first pulse occurring during the initial period. Accordingly, in the case of the monitored parameter being the time from the beginning of the pulse to the instant at which the output voltage reaches the above-mentioned voltage threshold, the next pulse may have the same ON-time as the first pulse, or the above-mentioned subsequent period may be commenced. In other words, according to whether a predetermined condition associated with the monitored electrical parameter occurs in the first or a subsequent pulse of the initial period, the treatment cycle may consist of one pulse of predetermined duration or a plurality of pulses having the same predetermined duration, each pulse being followed by an OFF-time of a predetermined length.

Other electrical parameters may be monitored to determine when the initial period of the treatment cycle ends, for example, the absolute or fractional difference between the instantaneous power amplitude achieved prior to the output voltage reaching the preset voltage threshold and the instantaneous power amplitude at the end of the pulse, or the sensed load resistance. In either case, the parameter is monitored during each pulse of the initial period in order to determine when the pulsing pattern of the initial period (i.e. characterised by the predetermined ON-time and predetermined OFF-time) should be terminated.

One advantage of the invention is illustrated when attempting to coagulate vessels immersed in blood or other conductive fluid. With conventional bipolar generators, the presence of blood causes current to be dissipated into the blood rather than into the tissue or bleeding vessel. This is due to blood conducting the current better than the tissue between the two jaws, a situation which will create current hogging. This means that, to achieve haemostasis, the current must be applied for a long period of time, thereby ensuring hot spots, charring and sticking. Using the present system, the bipolar r.f. energy pulses are applied for very short periods of time, and the formation of vapour prevents the current hogging. This ensures that the tissue receives sufficient energy to achieve haemostasis, and is not preferentially dissipated into the blood as a result of hot spots.

The features of the present system are particularly useful when performing endoscopic surgery, wherein vascular structures require division or dissection in a bloodless fashion. Typical procedures include laparoscopic procedures, such as laparoscopic assisted vaginal hysterectomy and laparoscopic supracervical hysterectomy wherein the uterine and other associated vessels require division; laparoscopic Nissen fundoplication, where the short gastric and other associated vessels require division; laparoscopic procedures on the bowel, where often the mesenteric vessels require division; laparoscopic appendicectomy, where the appendiceal artery and other associated vessels require division; mobilisation of the omentum where the omental vessels require division; laparoscopic bipolar tubal ligation, where the fallopian tube is coagulated to induce sterility; and, in general, for the division of vascular adhesions. In all cases, the cauterisation can be achieved without protracted dissection of the vascular structures to skeletonise them prior to sealing and division.

Other exemplary endoscopic procedures include minimal access cardiac surgery, where vascular structures (such as the internal mammary artery or gastroepiploic artery) are mobilised by division of branches prior to bypass; and the harvesting of other vascular structures (such as the saphenous vein) where once again the tributaries require division.

The present invention is not restricted to use with bipolar forceps. It may be used to advantage in other bipolar instrumentation to effect coagulation. The two poles of such an instrument, such as bipolar dissecting hooks, are often in close proximity, such that any conductive material between the hooks creates the shortest conductive path with limited penetration of the energy to the tissue against which the instrument is applied. By interrupting the current path directly between the hooks, as a result of vapour formation, a greater effect may be obtained in the tissue compared to conventional outputs.

Open surgical instruments such as bipolar forceps and the like may be used.

In the preferred embodiment described above, the application of r.f. power to produce the desired clinical effect is performed with a minimum burst energy capable of creating vapour within the grasped tissue. In particular, the burst energy is high enough to create vapour from the first burst when tissue is thin. This energy is delivered at a power sufficiently high that voltage clamping takes place within the burst, a thermal relaxation time before the next burst of at least 100 ms being allowed.

What is claimed is:

1. An electrosurgical generator comprising a source of radio frequency (r.f.) energy, at least a pair of output terminals for connection to a bipolar electrosurgical instrument and for delivering r.f. energy from the source to the instrument, and a pulsing circuit for the source, wherein the pulsing circuit and the source are so arranged as to deliver into a resistive load, when connected across the output terminals, an amplitude-modulated r.f power signal in the form of a succession of pulses, which succession is characterised by successive pulses being of progressively decreasing power amplitude and of progressively increasing pulse width.

2. A generator according to claim 1, wherein the increase in the pulse width of successive pulses is related to the decrease in amplitude.

3. A generator according to claim 2, wherein the increase in pulse width and decrease in power amplitude is such that the energy delivered in each pulse is substantially fixed from pulse to pulse.

4. A generator according to claim 1, including control circuitry including means for monitoring at least one electrical parameter associated with the output terminals, the decrease in the pulse amplitude and the increase in the pulse width being effected in response to the at least one electrical parameter.

5. A generator according to claim 4, wherein the at least one parameter is the resistance of the load.

6. A generator according to claim 4, wherein the generator includes circuitry for limiting the voltage applied to the load to a predetermined maximum value, and wherein the at least one parameter is the time from the start of the pulse for the voltage to reach the said predetermined maximum value.

7. A generator according to claim 6, wherein the predetermined maximum voltage value is below 200V peak.

8. A generator according to claim 1, wherein the pulse repetition rate is less than 1 Hz.

9. A generator according to claim 1, characterised in that the pulses are separated by periods of at least 100 ms in which the delivered power is substantially zero.

10. A generator according to claim 1, wherein the initial pulse width is in the range of from 25 ms to 750 ms.

11. A generator according to claim 1, wherein the succession of pulses is terminated by a period of continuous energy delivery.

12. A generator according to claim 11, wherein the period of continuous energy delivery is at least 1 second in duration.

13. A generator according to claim 1, wherein the depth of amplitude modulation in the said r.f. signal is at least 90% and the initial pulse mark-to-space ratio is less than 2:3.

14. A generator according to claim 1, arranged such that the pulsing frequency remains constant at a predetermined value over the major part of the said succession of pulses.

15. A generator according to claim 1, arranged such that at least one of the initial pulse mark-to-space ratio, the initial pulse width, and the pulsing frequency is automatically preset at the start of the said succession of pulses to a value which is dependent on an instrument identification signal received by the generator.

16. A generator according to claim 1, arranged such that at least one of the pulse mark-to-space ratio, the pulse width, and the pulsing frequency is automatically preset at the start of the said succession of pulses to a value which is dependent on the load resistance cross the output terminals at the said start.

17. A generator according to claim 1, arranged so as to be capable of delivering a peak power of at least 100W into any resistive load connected across the generator output in the range of from 20 ohms to 250 ohms.

18. An electrosurgical system comprising the combination of an electrosurgical generator as claimed in claim 1 and a bipolar electrosurgical instrument coupled to an output of the generator.

19. A system according to claim 18, wherein the instrument comprises a pair of forceps.

20. A system according to claim 18, wherein the instrument is removably connectible to the generator and includes an instrument identification element, and wherein the generator includes a sensing circuit for sensing the identification element, the pulsing circuit of the generator being arranged automatically to adjust the pulse width or mark-to-space ratio if the said succession of pulses in response to the identification element as sensed by the sensing circuit.

21. A system according to claim 20, wherein the identification elements, the sensing circuit and/or the pulsing circuit are selected and configured to decrease the pulse frequency when an instrument with a comparatively large tissue contact area is selected.

22. A system according to claim 20, comprising a plurality of bipolar electrosurgical forceps instruments which are selectively connectible to the generator and contain respective identification elements, wherein the electrodes of the instruments define different tissue contact areas, and wherein the respective identification elements, the sensing circuit and/or the pulsing circuit and selected and configured to set the said pulse width or mark-to-space ratio to a lower value for an instrument with electrodes defining a comparatively large tissue contact area to a higher value for an instrument with electrodes defining a comparatively small tissue contact area.

23. An electrosurgical generator comprising a source of radio frequency (r.f.) energy, at least a pair of output terminals for connection to a bipolar electrosurgical instrument and for delivering r.f. energy from the source to the instrument, and a pulsing circuit for the source, wherein the pulsing circuit and the source are arranged such that the r.f. energy is delivered over a period of time constituting a treatment cycle in which, when a resistive load is connected across the output terminals, is delivered as an amplitude-modulated r.f. power signal in the form of a succession of pulses in which the periods between successive pulses are at least 300 ms, the depth of amplitude modulation is at least 90%, the pulse mark-to-space ratio increases progressively from a value less than 2:3 at the start of the treatment cycle, and the pulse repetition rate is less than 1 Hz, wherein a sensing circuit is arranged to detect an initial value of a load impedance associated with the start of the treatment cycle, and wherein the pulsing circuit is arranged such that the initial pulse mark-to-space ratio increases with increasing sensed initial load impedance.

24. A method of electrosurgically coagulating tissue between the electrodes of a bipolar electrosurgical instrument, in which r.f energy is applied to the tissue via the electrodes in a succession of pulse bursts of progressively increasing length and progressively decreasing amplitude.

25. A method according to claim 24, wherein the increase in length of successive bursts is related to the decrease in amplitude of those bursts.

* * * * *